US008324279B2

(12) United States Patent
Anziano

(10) Patent No.: US 8,324,279 B2
(45) Date of Patent: Dec. 4, 2012

(54) COMPOSITIONS AND METHODS FOR INHIBITING AN ISOFORM OF HUMAN MANGANESE SUPEROXIDE DISMUTASE

(75) Inventor: Paul Q. Anziano, Philadelphia, PA (US)

(73) Assignee: MitoTek, LLC, Dover, DE (US)

( * ) Notice: Subject to any disclaimer, the term of this patent is extended or adjusted under 35 U.S.C. 154(b) by 31 days.

(21) Appl. No.: 12/562,033

(22) Filed: Sep. 17, 2009

(65) Prior Publication Data

US 2010/0028348 A1 Feb. 4, 2010

Related U.S. Application Data

(63) Continuation of application No. 10/858,450, filed on May 28, 2004, now abandoned.

(60) Provisional application No. 60/473,458, filed on May 28, 2003.

(51) Int. Cl.
*A01N 37/12* (2006.01)
*A01N 37/44* (2006.01)
*A01N 43/00* (2006.01)
*A01N 37/18* (2006.01)
*A61K 31/195* (2006.01)
*A61K 31/44* (2006.01)
*A61K 31/165* (2006.01)

(52) U.S. Cl. ................... 514/563; 514/357; 514/617

(58) Field of Classification Search .................. 514/563, 514/357, 617
See application file for complete search history.

(56) References Cited

U.S. PATENT DOCUMENTS

| | | | |
|---|---|---|---|
| 4,933,324 A | 6/1990 | Shashoua | |
| 4,939,174 A | 7/1990 | Shashoua | |
| 5,013,759 A | 5/1991 | Berman | |
| 5,112,863 A | 5/1992 | Hashimoto et al. | |
| 5,202,357 A | 4/1993 | Bowser et al. | |
| 5,284,876 A | 2/1994 | Shashoua et al. | |
| 5,540,911 A | 7/1996 | Hartman et al. | |
| 5,618,955 A | 4/1997 | Mechoulam et al. | |
| 6,107,499 A | 8/2000 | Shashoua | |
| 6,258,836 B1 | 7/2001 | Shashoua | |
| 6,407,137 B2 | 6/2002 | Shashoua | |
| 6,602,902 B2 | 8/2003 | Shashoua et al. | |
| 6,713,511 B1 | 3/2004 | Yehuda | |
| 6,737,506 B1 * | 5/2004 | Anziano | 530/300 |
| 7,144,994 B2 | 12/2006 | Anziano | |
| 7,227,001 B2 | 6/2007 | Anziano | |
| 2004/0122089 A1 | 6/2004 | Martin et al. | |
| 2004/0209959 A1 | 10/2004 | Hogestatt et al. | |
| 2004/0242655 A1 | 12/2004 | Anziano | |
| 2006/0025385 A1 | 2/2006 | Atlas | |
| 2008/0287548 A1 | 11/2008 | Anziano | |

FOREIGN PATENT DOCUMENTS

| | | |
|---|---|---|
| WO | WO 99/43697 A1 | 9/1999 |
| WO | WO 2004/069146 A2 | 8/2004 |
| WO | WO 2006/086422 A2 | 8/2006 |

OTHER PUBLICATIONS

Mukhopadhyay et. al. (Journal of the American College of Cardiology (2007) 50:528-536).*
Bisogno et. al. (Biochem. J. (2000) 351:817-824).*
Anguera, Montserrat C., et al. Methenyltetrahydrofolate Synthetase is a High-Affinity Catecholamine-Binding Protein, Arch Biochem Biophys, Nov. 15, 2006; 455(2) 175-187.
DiMarzo, Vincenzo, et al., Interactions between synthetic vanilloids and the endogenous cannabinoid system, FEBS Letters, vol. 436, Issue 3, pp. 449-454 (1998).
NCBI Pub Chem Database; CID11560744 dated Oct. 26, 2006.
Winstanley, Keith J., et al., Ortho-Substituted Catechol Derivatives: The Effect of Intramolecular Hydrogen-Bonding Pathways on Chloride Anion Recognition, J. Org. Chem. 2007, 72, 2803-2815.
NCBI Pub Chem Database; CID13309825 dated Feb. 8, 2007.
NCBI Pub Chem Database; CID11996946 dated Feb. 5, 2007.
NCBI Pub Chem Database; CID20250866 dated Dec. 5, 2007.
Bezuglov, V, et al., "Synthesis and biological evaluation of novel amides of polyunsaturated fatty acids with dopamine," Bioorganic &Medicinal Chemistry Letters, Pergamon, Elsevier Science, GB, vol. 11, No. 4, Feb. 26, 2001 pp. 447-449.
Di Marzo, V., et al., "Cannabimimetic fatty acid derivatives in cancer and inflammation," Prostaglandins &Other Lipid Mediators APR 2000, vol. 61, No. 1-2, Apr. 2000, pp. 43-61.
Melck, D., et al., "Unsaturated long-chain N-acyl-vanillyl-amides (N-AVAMs): vanilloid receptor ligands that inhibit anandamide-facilitated transport and bind to CB1 cannabinoid receptors." Biochemical and Biophysical Research Communications Aug. 19, 1999, vol. 262, No. 1, Aug. 19, 1999, pp. 275-284.
Pitkanen, Sari, et al., "Mitochondrial Complex I Deficiency Leads to Increased Production of Superoxide Radicals and Induction of Superoxide Dismutase," J. Clin. Invest., vol. 98, No. 2, Jul. 1996, 345-351.
Remington's Pharmaceutical Sciences, 17th ed., Mack Publishing Company, Easton, PA, 1985, p. 1418.
Robinson, B. H., "The Role of Manganese Superoxide Dismutase in Health and Disease," J. Inher. Metab. Dis. 21 (1998) 598-603.
Roche, Edward B., (ed.) "Bioreversible Carriers in Drug Design," American Pharmaceutical Association and Pergamon Press, 1987 (voluminous).
Sil, et al., "Myotrophin in human cardiomyopathic heart," Circulation Res. (1993) 73:98-108.
Sparano, "Cardiac toxicity of trastumazumab (herceptin): implications for the design of adjuvant trials," Sem. Oncol. (2001) 28 (Supp 3):20-27.
Straiker, et al., "Cannabinoids, Electrophysiology and Retrograde Messengers: Challenges for the Next 5 years," The AAPS J. (2006) 8(2) Art. 31, E272-276.
Suzuki and Evans, "Regulation of cardiac myocyte apoptosis by the GATA-4 transcription factor," Life Sci. (2004) 74:1829-1838.
Szeto, H.H., Mitochondria-Targeted Peptide Antioxidants: Novel Neuroprotective Agents, AAPSJ, (2006), 8 (3) 521-31, Arlington, VA.

(Continued)

*Primary Examiner* — Marcos Sznaidman
(74) *Attorney, Agent, or Firm* — Tara L. Rachinsky; Fox Rothschild LLP

(57) ABSTRACT

The present invention is directed to methods of modulating the activity of an isoform of manganese superoxide dismutase which is useful for the treatment of diseases such as heart failure.

3 Claims, 6 Drawing Sheets

OTHER PUBLICATIONS

Viera, et al., "Oxidized LDLs alter the activity of the ubiquitin-proteasome pathway: potential role in oxidized LDL induced apoptosis," FASEB J. (2000) 14:532-542.

Wiczk, et al., "Mechanism of fluorescence quenching of tyrosine derivatives by amide group," Chemical Physics Letters (2001) 341: 99-106.

U.S. Office Action dated Aug. 13, 2008 issued for U.S. Appl. No. 10/858,450.

U.S. Office Action dated Mar. 17, 2009 issued for U.S. Appl. No. 10/858,450.

U.S. Office Action dated Jul. 2, 2009 issued for U.S. Appl. No. 10/858,450.

U.S. Office Action dated Dec. 8, 2009 issued for U.S. Appl. No. 11/815,882.

European Supplemental Search Report dated Mar. 25, 2010 for European Patent Application No. 06734544.7.

European Office Action dated Mar. 15, 2010 in EP Application No. 04753806.1.

Eaton, et al., "Formation of 4-hydroxy-2-nonenal-modified proteins in ischemic rat heart," Am, J. Physiol. (1999) 276:H935-H943.

Office Action dated Feb. 22, 2011 issued in Canadian patent Application No. 2527024.

Patent Office Communication (Examiner's Report) dated Sep. 13, 2010 issued in Australian patent Application No. 2006212738.

Office Action dated Oct. 1, 2010 issued in U.S. Appl. No. 11/815,882.

Anziano, et al., "Expression of an isoform of magnesium superoxide dismutase in a child with multiple deletions of the human mitochondrial DNA," Pediatrics Res. (2000) 47:238A.

Alexander, et al., "Mechanism of Carbamate Inactivation of FAAH: Implications for the Design of Covalent Inhibitors and in Vivo Functional Probes for Enzymes," J . Chembiol. (2005) 12:1179-1187.

Aries, et al., "Essential role of GATA-4 in cell survival and drug-induced cardiotoxicity," Proc. Natl. Acad. Sci. USA (2004) 101:6975-6980.

Arola, et al., "Acute doxorubicin cardiotoxicity involves cardiomyocyte apoptosis," Cancer Res. (2000) 60:1789-1792.

Bacot, et al., "Covalent binding of hydroxy-alkenals 4-HDDE, 4-HHE, and 4-HNE to ethanolamine phospholipid subclasses," J. Lipid Res. (2003) 44:917-926.

Bezuglov V, et al., "Synthesis and biological evaluation of novel amides of polyunsaturated fatty acids with dopamine," Bioorganic & Medicinal Chemistry Letters, Pergamon, Elsevier Science, GB, vol. 11, No. 4, Feb. 26, 2001 pp. 447-449.

Bisogno et. al.,"N-acyl-dopamines: novel U synthetic CB(1) cannabinoid-receptor ligands and inhibitors of anandamide inactivation with cannabimimetic activity in vitro and in vivo," The Biochemical Journal, Nov. 2000,351 Pt 3,817-824.

Bisogno, T., et al., "Arachidonoylserotonin and other novel inhibitors of fatty acid amide hydrolase," Biochemical and Biophysical Research Communications, vol. 248, No. 3, Jul. 30, 1998, pp. 515-522.

Boger, et al., "Exceptionally potent inhibitors of fatty acid amide hydrolase: the enzyme responsible for degradation of endogenous oleamide and anandamide," Proc. Natl. Acad. Sci. USA (2000) 97:5044-5049.

Borg, et al., "Recognition of extracellular matrix components by neonatal and adult cardiac myocytes," Dev. Biol. (1984) 104:86-9.

Brame, et al., "Identification of extremely reactive gamma-ketoaldehydes (isolevuglandins) a products of the isoprostane, pathway and characterization of their lysyl protein adducts," J. Biol. Chem. (1999) 274:13139-13146.

Bugaisky, et al., "Differentiation of adult rat cardiac myocytes in cell culture," Circulation Res. (1989) 64:493-500.

Cracowski, et al., "Vascular biology of the isoprostanes," J. Vasc. Res. (2001) 38:93-103.

De Petrocellis, L., et al., "Endocannabinoids and fatty acid amides in cancer, inflammation and related disorders," Chemistry and Physics of Lipids 2000 IE, vol. 108, No. 1-2, 2000, pp. 191-209.

Deutsch, D.G., Glaser, S.T., Howell, J.M., et al. The cellular uptake of anandamide is coupled to its breakdown by fatty-acid amide hydrolase. J Biol Chem 276(10) 6967-6973 (2001).

Di Marzo, V., et al., "Cannabimimetic fatty acid derivatives in cancer and inflammation," Prostaglandins & Other Lipid Mediators APR 2000, vol. 61, No. 1-2, Apr. 2000, pp. 43-61.

European Supplemental Search Report dated Jul. 15, 2009 for European Patent Application No. 04753806.1.

Fajardo, et al., "Endocannabinoid Inhibition: A New Cardioprotective Strategy Against Doxorubicin Cardiotoxicity," J. American College of Cardiology (2007) 50(6):537-539.

Fegley, D., Kathuria, S., Mercier, R., et al. Anandamide transport is independent of fatty-acid amide hydrolase activity and is blocked by the hydrolysis-resistant inhibitor AM1172. Proc. Nat. Acad. Science (2004) 101:8756-8761.

Gewies, A., et al., "Cytochrome c Is Involved in Fas-mediated Apoptosis of Prostatic Carcinoma Cell Lines," Cancer Research, 60:2163-2168; 2000.

Greene, T.W., et al., "Protective Groups in Organic Synthesis," 3rd Edition, John Wiley & Sons, Inc., 1999 (voluminous).

Grune and Davies, "The proteasomal system and HNE-modified proteins," Mol. Aspects Med. (2003) 24:195-204.

Higuchi, T., et al., "Pro-drugs as Novel Delivery Systems," vol. 14 of the A.C.S. Symposium Series, 1974, (voluminous).

Hoff, H. F., et al., "Oxidation of LDL: Role in Atherogenesis," Klin Wochenschr (1991) 69:1032-1038.

International Search Report and Written Opinion dated Sep. 15, 2006 for International Application No. PCT/US2006/004354.

International Search Report and Written Opinion dated Mar. 14, 2005 for International Application No. PCT/US2004/017053.

Janssen, "The pulmonary biology of isoprostanes," Chem. Phys. Lipids (2004) 128:101-116.

Janusz, J., et al., "Vanilloids. 1. Analogs of capsaicin with antinociceptive and antiinflammatory activity," Journal of Medicinal Chemistry, Sep. 1993, 36(18), 2595-2604.

Khanolkar, A.D., Makriyannis, A. Structure-activity relationships of anandamide, an endogenous cannabinoid ligand. Life Sci 65 607-616 (1999).

Keefe, "Trastuzumab-associated cardiotoxicity," Cancer (2002) 95:1592-1600.

Kemp, et al, "Organic Chemistry," (1980) Worth Publishers, Inc. NY. (voluminous).

Kitta, et al., "Hepatocyte growth factor induces GATA-4 phosphorylation and cell survival in cardiac muscle cells," J. Biol. Chem. (2003) 278:4705-4712.

Li, Yibling, et al., "Dilated Cardiomyopathy and Neonatal Lethality in Mutant Mice Lacking Manganese Superoxide dismutase," Nature Genetics, vol. 11, Dec. 1995.

March, J., "Advanced Organic Chemistry," 4th Edition, John Wiley & Sons, Inc., 1992 (voluminous).

* cited by examiner

A.

kDa    1  2  3  4  5
47.5

32.5

25
18.5            ⊢MnSOD E3-
                              deleted isoform.

B.

kDa    1    2

32.5

25
18.5

1 2 3 4 5 6 7 8

MnSOD Exon3-deleted isoform peroxidative activity

A.

B.

ROS-generating
"Activity blot":
antibody shift

C.

MnSOD E3-
deleted
isoform

−    +    : anti-MnSOD
polyclonal
antibody

COMPOSITIONS AND METHODS FOR INHIBITING AN ISOFORM OF HUMAN MANGANESE SUPEROXIDE DISMUTASE

CROSS-REFERENCES TO RELATED APPLICATIONS

This application is a continuation of U.S. application Ser. No. 10/858,450, filed May 28, 2004, which claims the benefit of U.S. Provisional Application Ser. No. 60/473,458, filed May 28, 2003, the disclosure of each of which is incorporated herein by reference in its entirety.

FIELD OF THE INVENTION

The present invention is directed to methods of modulating oxidative damage to intracellular components such as mitochondrial DNA (mtDNA), mitochondrial lipids, and mitochondrial proteins. The present invention is also directed to modulating the activity of a spliced isoform of manganese superoxide dismutase.

BACKGROUND OF THE INVENTION

Manganese Superoxide Dismutase (MnSOD) is a component of the cellular antioxidant defense mechanism that is necessary for mitochondrial function, cellular energy production and cell viability. Native MnSOD is a mitochondrial protein that is imported from the cytoplasm and localized to the mitochondrial matrix, where it scavenges superoxide free radicals or anions and converts these reactive oxygen species into the benign oxidant, hydrogen peroxide ($H_2O_2$), and oxygen. MnSOD is expressed in all cell types and provides an essential function. MnSOD importance was clearly illustrated in mice neonatal offspring containing a homozygous disruption (knockout) of MnSOD gene. These mice develop multisystem, mitochondrial energy-loss pathologies that include cardiomyopathy, neurological and liver dysfunction and exhibit perinatal lethality. The homozygous MnSOD knock-out serves as a proof-of-principle for complete loss of MnSOD function.

The multisystem energy-loss phenotype in the MnSOD knockout mouse may be due to an adverse accumulation of superoxide free radicals within the mitochondria upon the onset of an aerobic environment, causing loss of the ATP-synthesizing capacity of mitochondria and either initiating premature cell death by necrosis or by initiating the mitochondrial membrane permeability transition, causing release of mitochondrial pro-apoptotic proteins from the mitochondria due to depolarization of the mitochondrial membrane. Adverse accumulation of superoxide will result in spontaneous dismutation of superoxide into hydrogen peroxide, which is normally a benign oxidant unless in the presence of a transition metal, which then initiates Fenton-type chemistry to generate reactive oxygen species similar to hydroxyl free radicals.

Research has shown that the MnSOD gene can express a splice isoform (isoMnSOD) during stress conditions that expresses a pro-oxidant form instead of the normal antioxidant activity of the normal MnSOD (Anziano, et al., Pediatrics Research, 47; 2000). IsoMnSOD is also described in WO 99/43697. MnSOD alternative splicing is inducible and depends on the deregulation of the normal MnSOD splicing pathway. Alternative splicing of the MnSOD RNA removes coding Exon 3, and fuses in-frame flanking Exons 2 and 4. The isoMnSOD protein is internally deleted for key alpha helical domain that serves in the parent MnSOD as a portal for the selective entry of superoxide anions into the MnSOD metal pocket. IsoMnSOD does not exhibit antioxidant, dismutase activity as the parent MnSOD, but exhibits in vitro a gain-of-function peroxidative activity that generates reactive oxygen free radicals from hydrogen peroxide ($H_2O_2$). In vivo, isoMnSOD initiates lipid peroxidation within the mitochondrial membrane and it causes modification of target proteins by oxidative stress markers such as the reactive lipid byproduct, 4-hydroxynonenal (HNE).

In addition, stress from internal factors (e.g. diseases) or by exogenous or external influences such as, for example, drugs, can impair a cell's and organism's viability. Although the pharmacological properties of drugs or potential drugs are well understood, companies still spend billions of dollars a year on candidates that fail during preclinical and clinical trials due to unforeseen drug toxicity. Current methods for predicting whether a drug will be toxic in an individual have not been particularly effective because there are few useful markers of drug-induced toxicity that would indicate whether a drug is worthwhile pursuing.

Additionally, there are numerous drugs that are used today whose effectiveness is diminished because of toxicity that is caused by inherent toxicity of the drugs, thereby limiting the useful dosage. Some of the toxicity that is caused by the drugs can be related to damage to mitochondrial contents due to altering and diminishing its antioxidant environment and, therefore, if the ancillary toxic event can be prevented it should enhance the effectiveness of the compounds.

In view of the above evidence, there is a need to identify modulators of isoMnSOD activity so that one can control the effects of isoMnSOD expression. There is also a need to identify compounds that can be used to reduce or prevent drug-induced toxicity. There are further needs for assays and methods that can be used to predict if a composition will cause drug-induced toxicity in an individual or a cell. The present invention helps to fulfill these needs as well as others.

SUMMARY OF THE INVENTION

The present invention provides methods of inhibiting an activity of isoMnSOD in a cell comprising contacting said cell with a compound of Formula I: Alk-$L^1$-$L^2$-D, wherein constituent members are defined herein.

In some embodiments, the present invention provides methods of treating drug-induced toxicity in an individual comprising administering to said individual a therapeutically effective amount of an isoMnSOD inhibitor.

The present invention also provides methods of treating heart failure in an individual comprising administering to said individual a therapeutically effective amount of an isoMnSOD inhibitor.

In some embodiments, the present invention provides methods of treating a mitochondrial related disease or condition in an individual comprising administering to said individual a therapeutically effective amount of an isoMnSOD inhibitor.

In some embodiments, the present invention provides methods of inhibiting cell death comprising contacting a cell with an isoMnSOD inhibitor, wherein said inhibitor does not modulate expression of a nucleic acid molecule encoding isoMnSOD.

The present invention also provides methods of inhibiting mitochondrial oxidative stress in a cell comprising contacting said cell with an isoMnSOD inhibitor.

In some embodiments, the present invention provides methods of inhibiting mtDNA damage in a cell comprising contacting said cell with an isoMnSOD inhibitor.

In some embodiments, the present invention provides methods of inhibiting production of reactive oxidative species (ROS) in a cell comprising contacting said cell with an isoMnSOD inhibitor.

The present invention also provides, methods of inhibiting lipid peroxidation in a cell comprising contacting said cell with an isoMnSOD inhibitor.

In some embodiments, the present invention provides methods of treating cancer comprising administering to a patient a chemotherapeutic and an isoMnSOD inhibitor.

The present invention also provides compositions comprising a chemotherapeutic and an isoMnSOD inhibitor.

In some embodiments, the present invention provides methods of identifying an isoMnSOD inhibitor comprising:
a) contacting a cell expressing isoMnSOD with a test compound;
b) measuring an isoMnSOD mediated event in said cell; and
c) comparing said isoMnSOD mediated event in said cell to a cell that has not been contacted with said test compound;

wherein a decrease in said isoMnSOD mediated event indicates that said test compound is an isoMnSOD inhibitor.

The present invention also provides methods of measuring toxicity of a compound comprising contacting said compound to a cell, wherein said cell comprises a nucleic acid molecule comprising a genomic fragment of MnSOD gene spanning Exon 2 to Exon 4 of said gene, wherein said fragment comprises a frameshift mutation in Exon 3, and is operably linked to a reporter gene, wherein expression of said reporter gene is indicative of compound being toxic.

DETAILED DESCRIPTION

Figure 1:
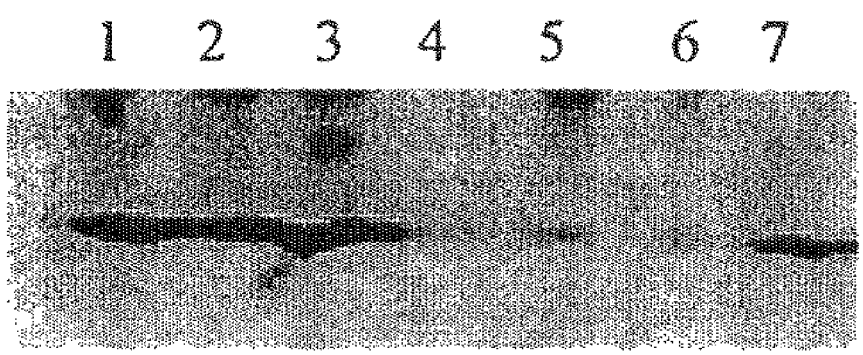
FIG. 1: Peroxidative assay of native mitochondrial extracts analyzed by the ROS-activity blot according to Example 13. Lane 1: no treatments; Lane 2: arachidonoyl-dopamine; Lane 3: eicosapentaenoyl (EPA)-dopamine; Lane 4: docosahexaenoyl (DHA)-dopamine; Lane 5: C18:4ω-3-dopamine; Lane 6: arachidonoyl-serotonin; Lane 7: no treatment.

Superoxide radicals and other highly reactive oxygen species are harmful by-products in every respiring cell, causing oxidative damage to a wide variety of macromolecules and cellular components. A group of metalloproteins known as superoxide dismutases (SOD) catalyzes the oxidation-reduction reaction that converts free-radical oxygen ($O_2^-$) to hydrogen peroxide ($H_2O_2$) and oxygen ($O_2$) and thus provides a defense mechanism against oxygen toxicity. SODs may contain manganese (Mn) or iron (Fe) or a combination of copper (Cu) and Zinc (Zn). SODs are described in U.S. Pat. No. 5,540,911.

Mitochondria are essential for meeting the body's acute and chronic energy demands because all cells of the body synthesize their fuel within the mitochondria. Mitochondrial DNA (mtDNA) contains thirteen genes encoding protein products that are necessary to synthesize the cell's fuel, adenosine triphosphate (ATP).

Diseases, drugs, or other factors that cause mitochondrial oxidative stress have often been implicated as an initiator of mitochondrial damage. If oxygen is not metabolized efficiently, oxygen free radicals can accumulate in the cell. Free radicals can cause damage to nucleic acid molecules, proteins or lipids. Since the mitochondria consume the most of the cell's oxygen, the mitochondria can be the most exposed organelle to free radical damage, especially mtDNA. If oxidative damage to mtDNA is left unrepaired, the point-mutation and deletion rate of the mtDNA increases, which may eventually lead to permanent organ fatigue.

An increase in mitochondrial mutations or an increase in free oxygen radicals can lead to an energy-loss syndrome which could effect the heart (cardiomyopathy or conduction disorders, e.g. heart failure), the nervous system, the pancreas (e.g., non-insulin dependent diabetes), the gastrointestinal tract (e.g., dysmotility or pseudo-obstruction), inner ear (e.g., sensorineural hearing loss), kidney (e.g. glomerulopathy) and/or the skeletal muscle (e.g., myopathy).

Because oxidative damage in cells can lead to various diseases, disorders, or conditions, there is an unfulfilled need to identify methods and compounds for treating diseases related to an increase in oxidative damage. The present invention helps to fulfill this need by identifying compounds that can inhibit or reduce isoMnSOD and, therefore, inhibit or reduce oxidative damage.

The recent discovery of an alternative splice form of MnSOD that has pro-oxidant activity and pro-apoptotic activity as compared to the antioxidant activity of MnSOD has led to the invention that oxidative damage caused by these species can be inhibited or reduced by compounds that inhibit or reduce an activity of isoMnSOD.

The present invention relates to the discovery that an alternative splice form of Manganese Superoxide Dismutase, hereinafter "isoMnSOD", is a pro-oxidant version of the normal splice form of Manganese Superoxide Dismutase, hereinafter "MnSOD". IsoMnSOD can be induced in all cell types, in all individuals, and is believed to be expressed in response to oxidative and mitochondrial damage. IsoMnSOD acts as a dominant, gain-of-function protein that when expressed at significant levels, induces mitochondrial dysfunction and mitochondrial energy-loss pathologies, including mitochondrial-mediated apoptotic cell death and acts as a modifier of an underlying genetic condition. IsoMnSOD generates oxygen free radicals other than superoxide in the presence of hydrogen peroxide and are not scavenged by native MnSOD. IsoMnSOD has been previously described in U.S. Pat. No. 6,737,506. The expression of isoMnSOD can lead to cell death and cellular toxicity. IsoMnSOD expression can be induced by drugs or compositions that have been shown to cause drug-related toxicity such as, for example, doxorubicin. The present invention describes methods and compositions that can be used, for example, to inhibit or reduce the activity of isoMnSOD, inhibit or reduce drug induced toxicity, and/or to inhibit or reduce cell death. The activity of isoMnSOD can also be modulated for the treatment of various mitochondrial related, energy-loss diseases, which are prone to oxidative damage of their remaining energy capacity.

Upon oxidative stress or mitochondrial damage isoMnSOD expression is increased by alternative splicing and has been found to not only create additional reactive oxidative species, but also to increase isoprostanes and HNE modifications of other proteins and itself. Isoprostanes are produced by the peroxidation of lipoproteins, which can be regulated by isoMnSOD. Elevated isoprostane levels have been associated with, for example, hepatorenal syndrome, rheumatoid arthritis, inflammation, atherosclerosis, inflammatory vascular diseases, and carcinogenesis (Jansenn, *Chemistry and Physics of Lipids,* 128 (2004) 101-116; Cracowski et al., *Journal of Vascular Research* 2001; 38:93-103; Eaton et al., *Am J Physiol.* 1999 March; 276(3 Pt 2):H935-43). Therefore, an increase in isoMnSOD activity can increase the risk of the patient of developing these and other conditions. The production of HNE can also lead to diseases or disorders by inactivating other proteins in the cell. Protein inactivation by HNE occurs because HNE covalently modifies enzymes in a cell which can assist in targeting proteins for degradation by the proteosome (Grune et al. Mol Aspects Med. 2003 August-October; 24(4-5):195-204). However, if when HNE is overproduced and causes the modification of a large number of proteins, clogging of the proteosome can result, which can inhibit the function of a cell and lead to cell death. Under normal circumstances HNE is metabolized and is prevented from damaging the cell. However, when HNE accumulates, in addition to clogging the proteosome, HNE can lead to atherogenesis (Hoff et al. Klin Wochenschr. 1991 Dec. 15; 69(21-23):1032-8). Therefore, inhibiting HNE production by inhibiting isoMnSOD according to the present invention can be beneficial to the cell.

Accordingly, in one aspect, the present invention provides methods of inhibiting or reducing an activity of isoMnSOD in a cell comprising administering an isoMnSOD inhibitor.

As used herein, the term "MnSOD" refers to the gene Manganese Superoxide Dismutase. "MnSOD" can also refer to either the cDNA, RNA, mRNA, genomic DNA, or gene product (e.g. protein) of the MnSOD gene. In some embodiments, "MnSOD" refers to the antioxidant form of MnSOD. "MnSOD" also refers to a cDNA, mRNA, or protein that comprises the third exon of the MnSOD gene.

As used herein, the term "isoMnSOD" or "alternative splice form of MnSOD" refers to a splice form the MnSOD gene that lacks exon 3. "IsoMnSOD" can also be referred to as "MnSOD-exon3-deleted", "exon 3 deleted MnSOD" or "altisoMnSOD". The genomic structure of MnSOD, nucleic acid sequence of isoMnSOD, and the amino acid sequence of isoMnSOD are described in U.S. Pat. No. 6,737,506. An exon 3 deleted MnSOD lacks the active site histidine at position 74 (74H; numbering based upon the mature form of native MnSOD, where the mitochondrial targeting signal in cleaved at K25 for both native MnSOD and isoMnSOD) that is required selective entry of superoxide into the native MnSOD active site and for manganese binding as well as the peptide sequences required for forming the final homotetrameric complex of antioxidant-MnSOD associated with superoxide capture, but molecular modeling of isoMnSOD has shown that histidine at position 31 (H31) is reoriented and now substitutes for 74H, with otherwise complete conservation of the positioning of active site amino acids in native MnSOD. The active site for isoMnSOD is more accessible to molecules larger than superoxide, such as $H_2O_2$. In some embodiments, "isoMnSOD" refers to polynucleotides that encode polypeptides or the polypeptides themselves that are defined by the above described structure/function parameters. In some embodiments, "isoMnSOD" refers to a polypeptide that has pro-oxidant activity.

An "activity of isoMnSOD" refers to the protein activity of the polypeptide encoded by the isoMnSOD transcript. In some embodiments, the activity is pro-oxidant activity of the isoMnSOD protein. Pro-oxidant activities include any activity that can lead to oxidation of cellular components and includes, for example, generating and/or facilitating the accumulation of reactive oxygen species as well as damaging nucleic acids, proteins, lipids, and the like by oxidation. The activity can also refer to isoMnSOD pro-apoptotic activity. The activity can also refer to the binding activity of a polypeptide comprising isoMnSOD. For example, the binding activity can refer to the ability of the protein to bind other polypeptides, reactive oxygen species (ROS), metals, transition metals, compounds, inhibitors, activators, or other co-factors.

An "isoMnSOD inhibitor" refers to a pharmaceutical agent such as, for example, a protein (e.g., antibody or other binding protein) or small molecule (compound) that is able to inhibit or reduce an activity of the isoMnSOD gene product. In some embodiments, the isoMnSOD inhibitor inhibits or reduces the pro-oxidant activity, the binding activity, both types of activity or other activity. The isoMnSOD inhibitor can also inhibit or reduce the binding of isoMnSOD to other polypeptides, to reactive oxygen species, to metals, to transition metals, co-factors, activators, inhibitors, or combinations thereof.

The isoMnSOD inhibitor or composition, such as a pharmaceutical composition, thereof can be administered to any cell expressing isoMnSOD either in vitro, in vivo, ex vivo, or combinations thereof. Methods of administration are well known to the skilled artisan and described herein. A composition comprising the isoMnSOD inhibitor and an acceptable carrier (such as a pharmaceutically acceptable carrier) or diluent may be formulated by one having ordinary skill in the art depending upon the chosen mode of administration. Suitable carriers are described in the most recent edition of *Remington's Pharmaceutical Sciences*, A. Osol, a standard reference text in this field.

The compositions according to the present invention may be administered as a single dose or in multiple doses. The compositions of the present invention may be administered either as individual therapeutic agents or in combination with other therapeutic agents.

The compositions or inhibitors of the present invention may be combined with conventional therapies, which may be administered sequentially or simultaneously. One or more additional agents such as, for example, anti-viral agents, antibodies, anti-inflammatory agents, chemotherapeutics, antibiotics, and/or immunosuppressants can be used in combination with the compounds of the present invention for treatment of drug induced toxicity or other conditions relating to an oxidative damage disorder. The agents can be combined with the present compounds in a single dosage form, or the agents can be administered simultaneously or sequentially as separate dosage forms.

The compositions comprising an isoMnSOD inhibitor may be administered by any means that enables the active agent to reach the agent's site of action in the cell or in the body of an individual. Because some compounds are subject to being digested, hydrolyzed or otherwise broken down when administered orally, parenteral administration (e.g., intravenous, subcutaneous, intramuscular) can be used to optimize absorption. In addition, the compositions of the present invention may be injected at a site at or near the oxidative damage. For example, administration may be by direct injection into tissue directly adjacent to the oxidative damage. If the individual to be treated is suffering from oxidative damage on the skin or drug-induced toxicity on the skin, the isoMnSOD inhibitor may be formulated with a topical carrier (such as a pharmaceutically acceptable topical carrier) and the formulation may be administered topically as, for example, a cream, a lotion, or an ointment.

The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of isoMnSOD inhibitor can be about 1 µg to 100 milligrams per kilogram of body weight. In some embodiments, about 0.5 to about 500, about 1 to about 400, about 1 to about 300, about 1 to about 200, about 1 to about 100, about 1 to about 50, about 1 to about 10 milligrams per kilogram per day is given in divided doses 1 to 6 times a day or in sustained release form in an effective to obtain desired results.

In some embodiments, the isoMnSOD inhibitor is administered in a therapeutically effective amount. As used herein, the term "therapeutically effective amount" is meant to refer to an amount of an isoMnSOD inhibitor which produces a clinical effect observed as reduction or reverse in drug related toxicity, clinical endpoints, or oxidative damage in an individual when a therapeutically effective amount of an isoMnSOD inhibitor is administered to an individual or to a cell. Therapeutically effective amounts are typically determined by the effect they have compared to the effect observed when a composition which includes no active ingredient is administered to a similarly situated individual. The precise effective amount for a subject will depend upon the subject's size and health, the nature and extent of the condition, and the therapeutics or combination of therapeutics selected for administration. However, the effective amount for a given situation is determined by routine experimentation and is within the judgment of the clinician.

As used herein, the term "contacting" refers to the bringing together of indicated moieties in an in vitro system or an in vivo system. For example, "contacting" a cell with an isoMnSOD inhibitor or another compound of the invention includes the administration of the isoMnSOD inhibitor to an individual or patient, such as a human, having an isoMnSOD protein, as well as, for example, introducing the isoMnSOD inhibitor into a sample containing a cellular or purified preparation containing the isoMnSOD protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the term "cell" refers to a cell that is either in vivo, in vitro, or ex vivo. The isoMnSOD inhibitor can be contacted with any type of cell including, for example, dividing cells, non-dividing cells, multinucleated cells, cancer cells, neural cells, muscle cells, heart cells, brain cells, digestive tract cells (e.g. stomach, small intestine, large intestine, esophagus, and the like), pancreas cells, and the like. In some embodiments, the cell is a non-dividing cell. In some embodiments, the cell is a heart cell.

The present invention also provides methods of inhibiting or reducing the production of free isoprostanes, HNE, and modification of proteins by HNE and/or isoprostanes. As discussed above, the accumulation of HNE and isoprostanes can be deleterious to a cell and an individual or be indicative cellular damage and disease. The expression and activity of isoMnSOD can lead to the accumulation of these two product or related products and, therefore, directly contribute to the modification of proteins which can result in the degradation of essential proteins that would otherwise not be degraded, but also can lead to the clogging of the proteosome and eventually to the death or dysfunction of a cell.

In some embodiments, the present invention provides methods of inhibiting or reducing isoprostane production in a cell comprising contacting the cell with an isoMnSOD inhibitor. In some embodiments, the isoprostane is, for example, 8-epi-$PGF_{2\alpha}$ or isolevuglandin (e.g. $\alpha$, $\nu$, and, $\delta$). In some embodiments, the inhibitor inhibits or reduces isoprostane protein modification.

As used herein, the term "isoprostane protein modification" refers to a covalent modification of a protein that occurs when the protein comes in contact with one or more isoprostane molecules. In some embodiments, the isoprostane modification inhibits or reduces an activity of a protein. The "activity of a protein" can be enzymatic or non-enzymatic (e.g. binding to another molecule, signal transduction, targeting of itself or another protein to a specific location or organelle within or outside a cell). In some embodiments, the protein is modified with an oxidized lipid or with an oxidized isolevuglandin, such as isolevuglandin-lysine adducts on apolipoprotein B. (Identification of Extremely Reactive γ-Ketoaldehydes (Isolevuglandins) as Products of the Isoprostane Pathway and Characterization of Their Lysyl Protein Adducts. JBC Vol. 274, pp. 13139-13146, 1999. Cynthia J. Brame, Robert G. Salomon, Jason D. Morrow, and L. Jackson Roberts).

In further embodiments, the present invention can be used to inhibit or reduce HNE production and/or HNE protein modification in a cell, for example, by contacting the cell with an isoMnSOD inhibitor. As used herein, the term "HNE protein modification" refers to a covalent modification of a protein that occurs when the protein comes in contact with one or more HNE molecules. In some embodiments the protein is modified by 4-hydroxy-2-nonenal. In some embodiments, the protein being modified is cytochrome c or an oxidase subunit of cytochrome c.

Since HNE and/or isoprostane production can lead to hepatorenal syndrome, rheumatoid arthritis, atherosclerosis, carcinogenesis, and other diseases, the present invention provides methods of treating diseases related to FNE and/or isoprostane production comprising administering to an individual a therapeutically effective amount of an isoMnSOD inhibitor. In some embodiments, the disease to be treated is hepatorenal syndrome, rheumatoid arthritis, atherosclerosis, or carcinogenesis. In some embodiments, the isoMnSOD inhibitor is combined with one or more compounds used to treat hepatorenal syndrome, rheumatoid arthritis, atherosclerosis, or carcinogenesis. In some embodiments, an isoMnSOD inhibitor is co-administered with statins (e.g. Lipitor™, Zocor™, Crestor™, Mevacor™, Pravachol™, and the like), ezetimibe (Zetia™), non-steroidal anti-inflammatory agents (NSAIDs; e.g. ibuprofen, COX-2 inhibitors, aspirin, acetaminophen, disease modifying anti-rheumatic drugs (DMARDs; e.g. methotrexate, leflunomide (Arava™), etanercept (Enbrel™), infliximab (Remicade™), adalimumab (Humira™), anakinra (Kineret™)), antimalarials, gold salts, sulfasalazine, d-penicillamine, cyclosporin A, cyclophosphamide, azathioprine, corticosteroids, dopamine, Misoprostol, renal vasoconstrictor antagonists, systemic vasoconstrictors, N-acetylcysteine, and the like.

Drugs such as doxorubicin and Herceptin™ have been shown to cause toxicity in individuals through a mechanism that would implicate isoMnSOD. As discussed, herein, many compounds cause adverse events in patients that are due to oxidative damage that can be facilitated through the expression and activity of isoMnSOD. Doxorubicin has been shown to induce and/or increase the expression of isoMnSOD (described herein) in cells such as, for example, heart cells. Therefore, the present invention provides methods of treating drug-induced toxicity in an individual comprising administering to the individual a therapeutically effective amount of an isoMnSOD inhibitor. In some embodiments, the toxicity is organ toxicity. Examples of organs that can be effected by drug induced toxicity include, but are not limited to, heart, pancreas, liver, kidney, brain, colon, stomach, and bone marrow. Drug toxicity can also affect the skin (e.g., leading to hair loss), the eye (e.g., leading to macular degeneration), and the nervous system (e.g., drug induced neural degeneration). In some embodiments, the drug-induced toxicity leads to heart failure.

According to another aspect of the invention, it provides methods of treating heart failure in an individual comprising administering to the individual a therapeutically effective amount of an isoMnSOD inhibitor. In some embodiments, the heart failure is ischemic or non-ischemic heart failure. In some embodiments, the heart failure is non-ischemic heart failure. In some embodiments, the heart failure is drug induced.

As used herein, the term "heart failure" refers to a condition initiated by impairment of the heart's function as a pump. Heart failure is a progressive disorder in which damage to the heart causes weakening of the cardiovascular system. It is clinically manifested by fluid congestion or inadequate blood flow to tissues. Heart failure progresses by inappropriate responses of the body to heart injury. Heart failure may be the sum of one or many causes. "Ischemia" is characterized by a decrease in the blood supply to a bodily organ, tissue, or part caused by constriction or obstruction of the blood vessels. Thus, "ischemic heart failure" refers to heart failure facilitated by a chronic or acute decrease in blood supply to the heart leading to necrotic cell death. In contrast, "non-ischemic heart failure" refers to damage to the heart that is not characterized by a decrease in the blood supply to the heart or caused by constriction or obstruction of the blood vessels. An example of non-ischemic heart failure is, but not limited to, oxidative damage to the heart. In some embodiments, non-ischemic heart failure is drug induced. An example drug that can lead to drug induced, non-ischemic heart failure is an anthracycline compound. Examples of anthracycline compounds include, but are not limited to, doxorubicin, epirubicin, daunorubicine, idarubicin, and anthracenedione (mitoxantrone). Non-ischemic heart failure can also be induced by chemotherapy, such as, for example, by treatment with nucleic acid damaging agents (e.g., DNA damaging agents) such as Topoisomerase II inhibitors, as well as non-nucleic acid damaging agents. Non-ischemic heart failure can also be induced by radiation (such as in combination with chemotherapy) and is an example of a nucleic acid damaging agent. A "nucleic acid damaging agent" refers to a compound or agent that causes damage to DNA or RNA. The compound or agent can cause damage to the nucleic acid molecule directly or indirectly. By "direct" damage to the nucleic acid molecule it is meant that the compound or agent modifies the nucleic acid molecule itself, rather than effecting another molecule which results in the damage of the nucleic acid molecule. A compound or agent that effects another molecule that results in damaging a nucleic acid molecule in the cell is said to "indirectly damage" the nucleic acid molecule. Examples of "agents" that can damage DNA are, but not limited to, radiation (e.g. gamma or ultraviolet), cytotoxins (e.g., chemotherapeutics), and the like.

Antibodies that recognize and inhibit proteins involved in tumorigenesis have been used to treat cancer, but can be toxic and in some instances lead to heart failure. Therefore, the present invention also provides for methods of treating heart failure (e.g. non-ischemic) induced by antibodies that are used to treat cancer. The type of cancer that is being treated can be any cancer including, for example, breast cancer, lung cancer (e.g., non-small cell), pancreatic cancer, colon cancer, prostate cancer, ovarian cancer, glioma and the like. An example of an antibody that can facilitate, lead to, or cause heart failure is an antibody that recognizes the protein HER-2 (e.g. Herceptin™). The HER-2 proto-oncogene (also known as erbB-2, c-neu and HER-2/neu) and its association with various cancers is known to one of ordinary skill in the art. The risk of heart failure in an individual treated with antibodies used to treat cancer in an individual is further increased if the antibody treatment is combined with a nucleic acid damaging agent such as, for example, a Topoisomerase II inhibitor (J. Sparano. *Semin Oncol* 28: 20-27 (2001)). Therefore, in some embodiments, methods of treating cancer include administration of either or both of a chemotherapeutic or antibody in combination with an isoMnSOD inhibitor.

Although the exact mechanism of how doxorubicin (Dox) increases the risk of heart failure is not clearly understood, it is believed that doxorubicin generates superoxide which is then converted into hydrogen peroxide in the presence or absence of MnSOD. At low concentrations of doxorubicin, little of the $H_2O_2$ accumulates in the mitochondria. While not wishing to be bound by theory, it is possible that native MnSOD scavenges all or most of the superoxide. Although the isoMnSOD is induced by doxorubicin and is present in the mitochondria, relatively little lipid peroxidation occurs. At higher concentrations of Dox, the Dox-generated superoxide is believed to overwhelm the endogenous native MnSOD (antioxidant) protein, allowing $H_2O_2$ to accumulate due to spontaneous dismutation of superoxide into $H_2O_2$. At these higher concentrations, isoMnSOD is believed to accept hydrogen peroxide and convert it into reactive oxygen species, which can result in oxidative damage including, but not limited to, lipid peroxidation, generation of HNE, generation of isoprostanes, and/or mitochondrial damage. In some instances, it is believed that the generated HNE can modify isoMnSOD. Thus, the HNE-modified isoMnSOD can be used as a marker of lipid peroxidation and presence of HNE, as well as antibodies directed against amino acid sequences of isoMnSOD, not restricted to the MnSOD E2/E4 junction, that can either detect reactive lipid byproducts and drugs modifications or have their binding reduced or blocked by amino acid modifications, including those at positions H26, H29, and K51. Accordingly, the inhibition of isoMnSOD can lead to a reduction in lipid peroxidation and reduce the toxicity of doxorubicin and other drugs that induce or increase the expression of isoMnSOD. Thus, in some embodiments, the present invention provides a method of inhibiting or reducing doxorubicin induced toxicity comprising administering to an individual a therapeutically effective amount of an isoMnSOD inhibitor.

The present invention also provides methods of treating mitochondrial related diseases or conditions in an individual comprising administering to said individual a therapeutically effective amount of an isoMnSOD inhibitor.

As used herein, the term "mitochondrial related disease" refers to a disease, condition, or disorder where the function of the mitochondria is disrupted. The function can be disrupted by mitochondrial DNA (mtDNA) damage, proteins functioning abnormally within the mitochondria, membrane depolarization, and the like. A "mitochondrial related disease" can also be referred to as an energy-loss disease because the mitochondria supplies the energy for the cell. A "mitochondrial related disease" can also be referred to as an premature cell death disease because loss of the mitochondrial energy supply can initiate necrosis or control the release of pro-apoptotic proteins into the cytoplasm. The expression of isoMnSOD disrupts the function of the mitochondria, such as by facilitating oxidative damage to the mitochondria, and can be therefore detrimental to the viability of a cell, tissue or individual. Thus, inhibiting or reducing the activity of isoMnSOD can improve the condition of a cell, tissue, or individual suffering from a mitochondrial related disease. In some embodiments, the mitochondrial related disease is characterized by abnormal levels of oxidative damage to the mtRNA. An example of a mitochondrial related disease is cardiomyopathy (e.g., non-ischemic heart failure) Additional examples are well known to those skilled in the art.

Another aspect of the present invention includes methods of inhibiting or reducing mitochondrial oxidative stress in a cell comprising contacting said cell with an isoMnSOD inhibitor. As used herein, the term "mitochondrial oxidative stress" refers to a condition in the cell in which the mitochondria is damaged by oxidative agents or a condition that produces oxidative agents that can cause damage to the mitochondria or to a cell. Mitochondrial oxidative stress includes, but is not limited to, conditions where the mitochondria or cell's antioxidant environment has been substantially altered or overwhelmed and contains abnormal amounts of reactive oxygen species. An example of a disease characterized by mitochondrial oxidative stress is drug-induced organ failure (such as drug induced heart failure). One of skill in the art can determine if a cell contains abnormal amounts of reactive oxygen species by comparing the cell or cells in question to a cell or cells that is known to be normal. Methods of measuring the presence or level of reactive oxygen species in a cell are known in the art.

In some embodiments, the present invention provides methods of inhibiting or reducing mtDNA damage in a cell comprising contacting the cell with an isoMnSOD inhibitor. "mtDNA damage" refers to damage to the DNA or nucleic acids present inside the mitochondria. Examples of mtDNA damage include, but are not limited to, mutations, deletions, insertions, cross-linkages, or other modifications that are not found in undamaged mtDNA. In some embodiments, mtDNA damage includes oxidative damage caused directly or indirectly by reactive oxygen species.

The present invention also provides methods of inhibiting or reducing cell death comprising contacting a cell with an isoMnSOD inhibitor. In some embodiments, the inhibitor does not include an inhibitor that modulates expression of a nucleic acid molecule encoding a polypeptide comprising isoMnSOD. In some embodiments, the cell death is necrotic or apoptotic cell death. In some embodiments, the cell death is caused by elevated levels of reactive oxygen species, lipid peroxidation, HNE, isoprostanes or the like.

In some embodiments, the isoMnSOD inhibitors of the present invention are administered to any cell that expresses isoMnSOD or may be likely to express isoMnSOD (such as, for instance, the cell will be contacted with chemotherapeutic). In some embodiments, the cell is a non-dividing cell, dividing cell, or a cell that is undergoing senescence. A "non-dividing cell" refers to cell that is no longer undergoing cell division (e.g. mitosis or meiosis). Examples of non-dividing cells include, but are not limited to, cardiomyocytes, hepatocytes, pancreatic cells, and the like.

As used herein the term "cell death" or "premature cell death" refers to the death of a cell through apoptosis (e.g. programmed cell death) or necrosis. The apoptosis can be regulated through a p53 dependent pathway or a p53 independent pathway.

In some embodiments, the present invention provides methods of inhibiting or reducing the production of reactive oxygen species (ROS) in a cell comprising contacting the cell with an isoMnSOD inhibitor. "Reactive oxygen species" refers to compounds or molecules that have a reactive oxygen moiety. When oxygen abstracts electrons from other molecules in the cell, reactive oxygen species (ROS) can be formed. This electron abstraction leaves donor molecules with unpaired electrons, causing them to become highly reactive radicals. Reactive Oxygen Species (ROS) is a term that collectively describes radicals and other non-radical reactive oxygen derivatives. These intermediates can participate in reactions giving rise to free radicals or that are damaging to organic substrates. Examples of radical containing reactive oxygen species include, but are not limited to, hydroxyl radicals (e.g., $OH^-$), superoxide (e.g., $O_2^-$), nitric oxide (e.g., NO), thyl (e.g., RS), peroxyl (e.g., $RO_2$), lipid peroxyl (e.g., LOO), and the like. Examples of non-radical containing reactive oxygen species include, but are not limited to, hydrogen peroxide (e.g., $H_2O_2$), hypochloric acid (e.g., HOCl), singlet oxygen (e.g., $^{-1}O_2$), ozone (e.g., $O_3$), lipid peroxide (e.g., LOOH), and the like (where R is H or alkyl, L is a lipid moiety). In some embodiments, the isoMnSOD inhibitor inhibits the production of radical containing reactive oxygen species, non-radical containing reactive oxygen species, or both.

Cell membranes, organelle membranes and other structures within the cell contain lipids that are essential for the viability of the cell. The lipids present in the cellular membranes can be damaged by oxidative species and, therefore, negatively impact the cell's viability. Lipid peroxidation of a cell can occur by the interaction of a lipid with a reactive oxygen species, which, in some embodiments, can be facilitated by a protein within the cell, such as, for example, isoMnSOD. Accordingly, another aspect of the present invention involves methods of inhibiting or reducing lipid peroxidation in a cell comprising contacting the cell with an isoMnSOD inhibitor. "Lipid peroxidation", as used herein, refers to the oxidative deterioration of one or more lipids containing any number of carbon-carbon double bonds.

As discussed above, isoMnSOD inhibitors can be combined with other pharmaceutical compositions, agents, or compounds when being administered to a cell or an individual. One class of compounds that can be co-administered with an isoMnSOD inhibitor are chemotherapeutics. Antibodies that recognize HER-2 (e.g. Herceptin™) and nucleic acid damaging agents, are compounds that can be co-administered with an isoMnSOD inhibitor. Herceptin™ has been a useful tool in the fight against breast cancer and in some cases is used in conjunction with chemotherapeutics including, but not limited to, Topoisomerase II inhibitors (e.g. doxorubicin, epirubicin, and the like). However, a HER-2 antibody or the combination of a HER-2 antibody and a Topoisomerase II inhibitor has been reported to increase the risk of heart failure (see, for example, Cancer. 2002 Oct. 1; 95(7):1592-600, which is herein incorporated by reference). This increase is related to an increase in oxidative damage in the heart. Accordingly, the present invention provides methods of treating cancer comprising administering to a patient a therapeutically effective amount of one or more chemotherapeutics and an isoMnSOD inhibitor. The present invention further provides methods of treating cancer comprising administering to a patient a therapeutically effective amount of an antibody and an isoMnSOD inhibitor. The present invention further provides methods of treating cancer comprising administering to a patient a therapeutically effective amount of a chemotherapeutic, an antibody, and an isoMnSOD inhibitor. The administration of an isoMnSOD inhibitor reduces the oxidative damage to the individuals cells exposed to the chemotherapeutic and/or antibody and, therefore, allow the anti-cancer drugs to be given with a reduced risk of heart failure or other damage that is caused by the drugs.

In some embodiments, an inhibitor of isoMnSOD is administered to an individual who has been identified in need of an isoMnSOD inhibitor (e.g. an individual susceptible to heart failure). In some embodiments, an individual is in need of an isoMnSOD inhibitor if the individual has been identified as at-risk for heart failure. In some embodiments, the heart failure is drug induced or caused by a cancer treatment (e.g. Herceptin™ with or without an anthracycline). An individual can also be in need of an isoMnSOD inhibitor if the individual has been identified as suffering from an oxidative disease, mitochondrial-related disease, mtDNA damage, HNE and/or isoprostane protein modification related disease (e.g artherosclerosis), too much lipid peroxidation, and the like.

As discussed previously, isoMnSOD inhibitors can be combined with any chemotherapeutic or anti-cancer drug. The term "chemotherapeutic" refers to any chemical compound such as a cytotoxin used to treat the disease generally known as cancer. In some embodiments, at least one isoMnSOD inhibitor is co-administered with at least one, at least two, at least three, at least four, at least five, at least six, at least seven, or at least ten chemotherapeutics. In some embodiments, one or more isoMnSOD inhibitors are co-administered with an antibody that recognizes HER-2 (e.g. Herceptin™), a nucleic acid damaging agent (e.g. Topoisomerase II inhibitor, doxorubicin, epirubicin, daunorubicin, idarubicin, or anthracenedione), or combinations thereof. The cancer to be treated can be any cancer including, but not limited to Hodgkin's lymphoma, non-Hodgkin's lymphoma, breast cancer, ovarian cancer, testicular cancer, acute leukemia, soft tissue sarcoma, lung cancer (e.g., non-small cell), bladder cancer, pancreatic cancer, gastric cancer, thyroid cancer, hepatoma, wilm's tumor, glioma, or neuroblastoma. In some embodiments, the cancer is breast cancer.

In some embodiments, the present invention provides a composition comprising one or more chemotherapeutics and one or more isoMnSOD inhibitors. In some embodiments, the present invention provides a composition comprising one or more antibodies and one or more isoMnSOD inhibitors. In some embodiments, the present invention provides a composition comprising one or more chemotherapeutics, one or more antibodies, and one or more isoMnSOD inhibitors. In some embodiments, the composition is a pharmaceutical composition. The enzyme fatty acid amide hydrolase (FAAH) is known to recognize and break down fatty acids and their derivatives. Therefore, in some embodiments, an isoMnSOD inhibitor, such as an inhibitor that may be subject to cleavage by FAAH, is co-administered with a FAAH inhibitor, which would prevent or inhibit the degradation of the isoMnSOD inhibitors by FAAH. Examples of FAAH inhibitors include, but are not limited to, 4-benzyloxyphenyl-n-butylcarbamate, CAY10400™, and the inhibitors described in Boger et al. (*PNAS*, 97(10):5044-5049, which is herein incorporated by reference in its entirety).

Example isoMnSOD inhibitors include, for example, compounds of Formula I:

or pharmaceutically acceptable salts or prodrugs thereof, wherein:

Alk is $C_{2-100}$ alkenyl or $C_{2-100}$ alkynyl, each optionally substituted by one or more $R^1$;

$L^1$ is O, S, CO, C(O)O, C(O)NR$^2$, SO, S(O)$_2$, S(O)NR$^2$, S(O)$_2$NR$^2$, NR$^2$, NR$^2$C(O)NR$^3$, or NR$^2$C(S)NR$^3$;

$L^2$ is absent, $C_{1-6}$ alkylenyl, $C_{2-6}$ alkenylenyl, or $C_{2-6}$ alkynylenyl, each optionally substituted by one or more $R^4$;

D is aryl or heteroaryl, each optionally substituted by one or more $R^5$;

$R^1$ and $R^4$ are each, independently, halo, cyano, nitro, $C_{1-6}$ alkyl, $C_{1-6}$ haloalkyl, $C_{2-6}$ alkenyl, $C_{2-6}$ alkynyl, aryl, heteroaryl, $C_{3-7}$ cycloalkyl, heterocycloalkyl, S(O)R$^6$, S(O)$_2$R$^6$, C(O)R$^6$, OR$^7$, SR$^7$, C(O)OR$^7$, NR$^8$R$^9$ or NR$^8$C(O)R$^6$;

$R^2$ and $R^3$ are each, independently, H, $C_{1-6}$ alkyl, $C_{2-6}$ alkenyl, $C_{2-6}$ alkynyl, $C_{1-6}$ haloalkyl, aryl, heteroaryl, $C_{3-7}$ cycloalkyl, heterocycloalkyl, arylalkyl, heteroarylalkyl; ($C_{3-7}$ cycloalkyl)alkyl or heterocycloalkylalkyl;

$R^5$ is halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO$_2$, OR$^{12}$, SR$^{12}$, C(O)R$^3$, C(O)NR$^{14}$R$^{15}$, C(O)OR$^{12}$, OC(O)R$^{13}$, OC(O)NR$^{14}$R$^{15}$, NR$^{14}$R$^{15}$, NR$^{14}$C(O)R$^{15}$, NR$^{14}$C(O)OR$^{12}$, S(O)R$^{13}$, S(O)NR$^{14}$R$^{15}$, S(O)$_2$R$^{13}$, or S(O)$_2$NR$^{14}$R$^{15}$;

$R^6$ is H, $C_{1-6}$ alkyl, $C_{2-6}$ alkenyl, $C_{2-6}$ alkynyl, $C_{1-6}$ haloalkyl, aryl, heteroaryl, $C_{3-7}$ cycloalkyl, heterocycloalkyl, arylalkyl, heteroarylalkyl, ($C_{3-7}$ cycloalkyl)alkyl, heterocycloalkylalkyl, or NR$^{10}$R$^{11}$;

$R^7$ is H, $C_{1-6}$ alkyl, $C_{2-6}$ alkenyl, $C_{2-6}$ alkynyl, $C_{1-6}$ haloalkyl, alkoxyalkyl, haloalkoxyalkyl, aryloxyalkyl, heteroaryloxyalkyl, cycloalkyloxyalkyl, heterocycloalkyloxyalkyl, aryl, heteroaryl, $C_3$-$C_7$ cycloalkyl, heterocycloalkyl, arylalkyl, heteroarylalkyl; ($C_{3-7}$ cycloalkyl)alkyl or heterocycloalkylalkyl;

$R^8$ and $R^9$ are each, independently, H, $C_{1-6}$ alkyl, $C_{2-6}$ alkenyl, $C_{2-6}$ alkynyl, $C_{1-6}$ haloalkyl, aryl, heteroaryl, $C_{3-7}$ cycloalkyl, heterocycloalkyl, arylalkyl, heteroarylalkyl; ($C_{3-7}$ cycloalkyl)alkyl or heterocycloalkylalkyl;

or $R^8$ and $R^9$ together with the N atom to which they are attached form a 3-, 4-, 5-, 6-, or 7-membered heterocycloalkyl group;

$R^{10}$ and $R^{11}$ are each, independently, H, $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_7$ cycloalkyl or heterocycloalkyl;

$R^{12}$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^{13}$ is H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; and $R^{14}$ and $R^{15}$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl; or or $R^{14}$ and $R^{15}$ together with the N atom to which they are attached form a 4-, 5-, 6- or 7-membered heterocycloalkyl group.

In some embodiments, Alk is $C_{2-50}$ alkenyl.

In some embodiments, Alk is $C_{4-30}$ alkenyl.

In some embodiments, Alk is $C_{16-20}$ alkenyl.

In some embodiments, Alk is $C_{17}$, $C_{18}$ or $C_{19}$ alkenyl.

In some embodiments, Alk is $C_{2-50}$ alkenyl comprising at least two double bonds.

In some embodiments, Alk is $C_{2-50}$ alkenyl comprising at least four double bonds.

In some embodiments, Alk comprises at least one bis-allylic methylene group.

In some embodiments, Alk comprises 1 to about 10 bis-allylic methylene groups.

In some embodiments, Alk comprises 2 to 5 bis-allylic methylene groups.

In some embodiments, Alk corresponds to the alkenyl group of a polyunsaturated fatty acid.

In some embodiments, $L^1$ is O, CO, C(O)O, C(O)$NR^2$, $NR^2$ or $NR^2$C(O)$NR^3$.

In some embodiments, $L^1$ is CO, C(O)O, C(O)$NR^2$ or $NR^2$.

In some embodiments, $L^1$ is C(O)$NR^2$.

In some embodiments, $L^2$ is absent or $C_{1-6}$ alkylenyl.

In some embodiments, $L^2$ is $C_{1-3}$ alkylenyl.

In some embodiments, D is phenyl, naphthyl, anthracenyl, phenanthrenyl, indanyl, indenyl, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, or indolinyl, each optionally substituted by one or more $R^5$.

In some embodiments, $R^5$ is halo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^{12}$ or $NR^{14}R^{15}$.

In some embodiments, $R^5$ is halo, $C_{1-6}$ alkyl, $C_{1-4}$ haloalkyl, CN, $NO_2$, $OR^{12}$ or $NR^{14}R^{15}$.

In some embodiments, $R^5$ is OH.

In some embodiments, $R^5$ is methoxy.

Further examples isoMnSOD inhibitors include arachidonoyl dopamine (AA-DA; Cayman Chemical, MI), arachidonoyl serotonin (AA-serotonin; Cayman Chemical, MI), eicosapentaenoyl dopamine (EPA-DA; Cayman Chemical, MI), docosahexaenoyl dopamine (DPH-DA; Cayman Chemical, MI), and C18:4(ω-3)-dopamine (International Technology Transfer Concepts), and the like, each of which was found to inhibit pro-oxidant activity of isoMnSOD according to at least one of the assays provided in the Examples.

Further examples of isoMnSOD inhibitors include arachidonoyl-5-methoxytryptamine (AA-MOT; Cayman Chemical, MI), eicosapentaenoyl-5-methoxytryptamine (EPA-MOT; Cayman Chemical, MI), N-(4-hydroxyphenyl)arachidonoylamide (AM404; Cayman Chemical, MI); eicosapentaenoyl serotonin; docosahexaenoyl serotonin; arachidonoyl tyramine; arachidonoyl phenethylamine, C18:3(ω-3)-dopamine; C20:3(ω-6)-dopamine; C22:5(ω-3)-dopamine, and the like.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "alkylenyl" refers to a divalent alkyl linking group.

As used herein, "alkenylenyl" refers to a divalent alkenyl linking group.

As used herein, "alkynylenyl" refers to a divalent alkynyl linking group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "arylalkyl" refers to an alkyl group substituted by an aryl group.

As used herein, "cycloalkylalkyl" refers to an alkyl group substituted by a cycloalkyl group.

As used herein, "heteroarylalkyl" refers to an alkyl group substituted by a heteroaryl group.

As used herein, "heterocycloalkylalkyl" refers to an alkyl group substituted by a heterocycloalkyl group.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an O-haloalkyl group. An example haloalkoxy group is $OCF_3$.

As used herein, "aryloxy" refers to —O-aryl.

As used herein, "heteroaryloxy" refers to —O-heteroaryl.

As used herein, "cycloalkyloxy" refers to —O-cycloalkyl.

As used herein, "heterocycloalkyloxy" refers to —O-heterocycloalkyl.

As used herein, "alkoxyalkyl" refers to alkyl substituted by alkoxy.

As used herein, "haloalkoxyalkyl" refers to alkyl substituted by haloalkoxy.

As used herein, "aryloxyalkyl" refers to alkyl substituted by aryloxy.

As used herein, "heteroaryloxyalkyl" refers to alkyl substituted by heteroaryloxy.

As used herein, "cycloalkyloxyalkyl" refers to alkyl substituted by cycloalkyloxy.

As used herein, "heterocycloalkyloxyalkyl" refers to alkyl substituted by heterocycloalkyloxy.

As used herein, the term "bis-allylic" is used as known in the art and refers to a metheylene group ($CH_2$) flanked by double bonds. For example, the $CH_2$ moiety of —CH=CH—$CH_2$—CH=CH— is a bis-allylic methylene group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as α-camphorsulfonic acid. Other resolving agents suitable for fractional crystallization methods include stereoisomerically pure forms of p-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention can also include tautomeric forms, such as keto-enol tautomers. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium, The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods.

Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are hereby incorporated by reference in their entirety.

Synthesis

IsoMnSOD inhibitors of Formula I, including salts, hydrates, and solvates thereof, can be prepared using known organic synthesis techniques and can be synthesized according to any of numerous possible synthetic routes.

The reactions for preparing compounds of Formula I can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of formula I can involve the protection and deprotection of various chemical groups. The need for protection and deprotection, and the selection of appropriate protecting groups can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Compounds of Formula I are commercially available (e.g., Cayman Chemical, MI) or can be prepared according to numerous preparatory routes known in the literature. For example, polyunsatuarated fatty acids (e.g., arachidonic acid, linoleic acid, linolenic acid, docosahexaenoic acid, eicosapentaenoic acid, C18:4(ω-3) fatty acid, C20:4(ω-3) fatty acid, C20:3(ω-6) fatty acid, C20:3(ω-3) fat acid, C22:5(ω-3) fatty acid, C22:4(ω-3) fatty acid, C22:4(ω-6) fatty acid, C22:3(ω-3) fatty acid, etc.) can be combined with arylamines, heteroarylamines, arylalkylamines, heteroarylalkylamines, etc. optionally in the presence of an acid or base to form the amide-linked ($L^1$=CONR$^2$) product of Formula I. The resulting amide bond can be further reduced in the presence of a suitable reducing agent such as hydrogen over Pd catalyst to form the corresponding amine-linked ($L^1$=NR$^2$) product of Formula I. Additionally, the fatty acids can be combined with arylhydroxides (e.g. phenols) optionally in the presence of an acid or base to form ester-linked ($L^1$=COO) compounds of Formula I which can, in turn, be reduced to form ether-linked ($L^1$=O) compounds of Formula I. Other coupling reactions between fatty acids or derivatives thereof and aryl or heteroaryl reagents are well known in the art and can form carbonyl, ureido, sulfonyl, sulfinyl, sulfonamide and other linkages useful in the preparation of compounds of Formula I. Example coupling reactions can be found in March, *Advanced Organic Chemistry, 4$^{th}$* ed. John Wiley & Sons, NY, 1992 and Kemp et al., *Organic Chemistry,* Worth Publishers, Inc. NY, 1980; each of which is incorporated herein by reference in its entirety.

In addition to the isoMnSOD inhibitors described herein, any isoMnSOD inhibitor can be used. The present invention provides methods for identifying isoMnSOD inhibitors using methods that are described herein and the Examples. One of skill in the art can identify an isoMnSOD inhibitor by isolating an isoMnSOD polypeptide and measuring the activity with and without a candidate compound. In some embodiments, the candidate compound will inhibit the pro-oxidant activity of isoMnSOD and would, therefore, be considered an inhibitor of isoMnSOD activity. In some embodiments, the compound reduces the pro-oxidant activity of isoMnSOD by at least 10%, at least 20%, at least 30%, at least 40%, at least 50%, at least 60%, at least 70%, at least 80%, at least 90%, at least 95%, at least 96%, at least 97%, at least 98%, at least 99%, or 100%. This assay can also be used to identify activators of isoMnSOD activity. Methods of measuring pro-oxidant activity are known in the art and are also described herein.

In some embodiments, an isoMnSOD inhibitor is identified by a method comprising contacting a cell expressing isoMnSOD with a test compound; measuring a isoMnSOD mediated event in the cell; and comparing the isoMnSOD mediated event in the cell to a cell that has not been contacted with the test compound; wherein a decrease in the isoMnSOD mediated event indicates that the test compound is an isoMnSOD inhibitor. An "isoMnSOD mediated event" refers to a process or phenotypic event that is regulated or facilitated by isoMnSOD. In some embodiments, an "isoMnSOD mediated event" is cell death, oxidation, lipid peroxidation, isoprostane production, HNE production, isoprostane protein modification, HNE protein modification, or the like. In some embodiments, the "isoMnSOD mediated event is not oxidation. In some embodiments, the test compound is an antibody, peptide, polypeptide, nucleic molecule, small molecule, and the like. In some embodiments the test compound is not a nucleic acid molecule. In some embodiments, the test compound is not a small molecule compound.

IsoMnSOD activity can also be measured in vivo or in vitro by its pro-apoptotic activity. Induction of the isoMnSOD protein can lead to the premature cell death by apoptosis or by another mechanism. Therefore, by using a cell that normally does not express isoMnSOD, one of skill in the art can identify inhibitors of isoMnSOD activity by inhibiting the premature cell death of a cell.

As a non-limiting example, one of skill in the art can transform or transfect a cell line that does not express isoMn-SOD or expresses isoMnSOD at a low level with a nucleic acid molecule that expresses the isoMnSOD gene and protein. The expression of isoMnSOD in the cell line can lead to a phenotypic change that is measurable such as, for example, cell viability, cell death markers (e.g. caspase cleavage and expression), gene expression, protein expression, protein cleavage, and the like. A compound can be tested as an inhibitor of isoMnSOD activity to determine if the compound has an effect on the phenotype that is observed due to the expression of isoMnSOD. If the compound reduces the effect that is observed, the compound is said to be an inhibitor. In contrast, this assay can also be used to identify activators of isoMnSOD activity by determining whether the compound increases the effects of isoMnSOD as measured by a phenotype. In some embodiments, the compound will be tested in a cell line that does not express isoMnSOD and compared to a cell line that expresses isoMnSOD to determine if the change in phenotype is specific for the expression of isoMnSOD.

In some embodiments, a compound is considered to be an isoMnSOD inhibitor if the compound reduces the effect of isoMnSOD by at least 10%, at least 20%, at least 30%, at least 40%, at least 50%, at least 60%, at least 70%, at least 80%, at least 90%, at least 95%, at least 96%, at least 97%, at least 98%, at least 99%, or 100%. In some embodiments, the compound reduces the pro-oxidant activity or pro-apoptotic activity of isoMnSOD by at least 10%, at least 20%, at least 30%, at least 40%, at least 50%, at least 60%, at least 70%, at least 80%, at least 90%, at least 95%, at least 96%, at least 97%, at least 98%, at least 99%, or 100%.

isoMnSOD inhibitors can also be identified using assays that measure isoMnSOD mediated HNE production, isoprostane production, or lipid peroxidation. A compound would be considered to be an isoMnSOD inhibitor if the compound inhibits the amount of HNE or isoprostanes produced in a cell or if the compound inhibits lipid peroxidation. In some embodiments, these assays are performed in a cell where isoMnSOD is exogenously produced.

As used herein, the term "exogenously produced" refers to protein, peptide, or nucleic acid molecule that is not normally expressed in a cell or was not originally part of the genome of a cell. A gene or protein can be exogenously produced by using a nucleic acid molecule such as, for example, a plasmid or a virus (e.g. retrovirus, DNA virus, adenovirus, adeno-associated virus, and the like). In some embodiments, the nucleic acid molecule is free of infectious particles.

IsoMnSOD inhibitors can also be identified using animal models that have drug induced toxicity, such as non-ischemic heart failure. For example, a mammal can be treated with one or more chemotherapeutics that causes toxicity in the mammal. A test compound can be administered in conjunction with the chemotherapeutic to determine if it reduces the drug-induced toxicity. In some embodiments, the drug-induced toxicity is non-ischemic heart failure. Inducing toxicity using doxorubicin in animal models has been previously performed, see, for example, Arola et al. *Cancer Research*, 60:1789-1792. Therefore, an individual or non-human animal that has been treated with doxorubicin can be treated with a compound to determine if it is an isoMnSOD inhibitor. A compound is said to be an isoMnSOD inhibitor if it reduces the toxicity of the drug by at least 10%, at least 20%, at least 30%, at least 40%, at least 50%, at least 60%, at least 70%, at least 80%, at least 90%, at least 95%, at least 96%, at least 97%, at least 98%, at least 99%, or 100%.

A compound can also be identified as an isoMnSOD inhibitor by determining if the compound can bind to the isoMnSOD protein. Methods for determining the binding of a compound to a protein are known to one of ordinary skill in the art and any routine method can be used. As non-limiting examples, the compounds can be labeled to see if the compound interacts with the polypeptide. Once the compound is contacted with an individual, cell or protein, a cross-linking agent can be used to determine if the compound binds to the protein. If a compound is found to bind to an isoMnSOD protein either in vivo or in vitro and it inhibits an activity of isoMnSOD it is considered to be an isoMnSOD inhibitor. If a compound is found to bind to an isoMnSOD protein either in vivo or in vitro and it activates an activity of isoMnSOD it is considered to be an isoMnSOD activator.

The present invention has also identified that isoMnSOD is induced under specific circumstances, which includes, but is not limited to, drug-induced toxicity. Therefore, the expression of isoMnSOD can be used as a marker of drug induced toxicity. The ability to identify compounds that cause toxicity would save time and money in the development of drugs by discarding drugs that are prohibitively toxic and pursuing compounds with little toxicity or acceptable levels of toxicity. Therefore, the present invention provides methods of measuring toxicity of one or more compounds by contacting the one or more compounds with a cell, wherein the cell contains a nucleic acid molecule having a genomic fragment of MnSOD gene spanning Exon 2 to Exon 4 of the MnSOD gene, wherein the genomic fragment comprises a frameshift mutation in Exon 3, and is operably linked to a reporter gene, wherein expression of the reporter gene is indicative of toxicity. The reporter gene will only be expressed if the alternative transcript form of isoMnSOD gene is expressed or in the case of a genomic fragment if the alternative splice event occurs. Under non-toxic conditions (e.g. the drug does not cause toxicity) the reporter gene will not be expressed due to the presence of the frameshift mutation located in Exon 3 or equivalent sequence. Under drug-inducing toxic conditions the cells machinery removes Exon 3 by an alternative splicing mechanism, thereby allowing the expression of the reporter gene. The detection of the reporter gene either by RNA expression (e.g. mRNA or RNA), protein expression or the protein's activity indicates that the drug is toxic. If the reporter gene is not expressed or the reporter gene's activity is not detected, the compound is considered to be non-toxic. Methods of detecting gene expression are known to one of ordinary skill in the art and include, but are not limited to, RT-PCR, northern blot, western blot, immunofluorescence, immunoprecipitation, and the like.

A "reporter gene" refers to any gene that is used as indication that the splicing event has occurred. In some embodiments, the reporter gene is a luciferase gene, β-galactosidase gene, a secreted alkaline phosphatase gene, or a fluorescent protein (e.g. green fluorescent protein (GFP), red fluorescent protein, cyan fluorescent protein, or yellow fluorescent protein), and the like. In some embodiments, the reporter gene can be a gene that is not expressed in the cell or is expressed at low levels, so that an increase in expression is detected. The reporter gene can be detected using any method including, but not limited to, Western blot (to measure the protein expression of the reporter gene), enzymatic activity of the reporter gene product, fluorescent microscopy (e.g. immunofluorescence), ultraviolet absorption, RT-PCR (to detect the presence of the reporter gene's RNA or mRNA), and the like. This method can also allow the screening of more than one compound to determine if compositions or compounds in combination with one another would produce toxic effects. In some embodiments the composition comprises at least one compound, at least two compounds, at least three compounds, at least four compounds, or at least five compounds. In some embodiments, the compound is a pharmaceutical composition comprising a drug. In some embodiments, the drug is a small molecule, antibody, nucleic acid molecule (e.g. DNA, RNA, or virus), and the like.

In addition to the reporter gene being present in a cell line and a compound is tested in vitro (e.g. in cell culture or test tube), a transgenic non-human animal can be created incorporating a nucleic acid molecule comprising a genomic fragment of MnSOD gene spanning Exon 2 to Exon 4 of said gene, wherein the fragment comprises a frameshift mutation in Exon 3, and is operably linked to a reporter gene. The production of non-human transgenic animal is well known to one of ordinary skill in the art and only requires routine experimentation (see, for example, Transgenic Animal Technology: A Laboratory Handbook $2^{nd}$ ed., Carl Pinkert, Academic Press (2002); Mouse Genetics and Transgenics: A Practical Approach, Oxford University Press (2000); and Gene Targeting: A Practical Approach $2^{nd}$ ed., Oxford University Press (2000). Upon the generation of a transgenic animal (e.g. mouse or rat) one or more compounds can be tested to determine if the compound induces the expression of the reporter gene. The expression of the reporter gene would be indicative of drug-induced toxicity.

In either the in vivo or in vitro systems the reporter gene may be expressed without being induced by the test compound. However, if a test compound were to increase the expression of the reporter gene, it would then be considered to be toxic. In some embodiments, a test compound is considered to be toxic if the test compound increases the expression of the reporter gene over the basal levels by at least 10%, by at least 20%, by at least 30%, by at least 40%, by at least 50%, by at least 60%, by at least 70%, by at least 80%, by at least 90%, by at least 100%, by at least 200%, by at least 300%. As used herein, the term "basal level" refers to the level of expression that occurs in a cell or animal that occurs without being contacted with a test compound.

In addition, to using a reporter gene, one of skill in the art could measure the expression of isoMnSOD mRNA, protein, activity of isoMnSOD, or combinations thereof to determine if a compound is toxic. The expression or activity of isoMnSOD can be compared in the absence and the presence of one or more test compounds. If the expression or activity of isoMnSOD is increased in the presence of one or more test compounds as compared to the expression of isoMnSOD in the absence of the one or more test compounds, the increase in expression is indicative of the one or more compounds being toxic. If the expression or activity of isoMnSOD is not increased in the presence of one or more test compounds, then the lack of increase in expression is indicative of the compound not being toxic.

In some embodiments, a change in expression or activity of isoMnSOD or of the above-mentioned reporter gene is indicative of the one or more test compounds being toxic if the expression or activity of isoMnSOD or the reporter gene is increased by at least 5%, at least 10%, at least 20%, at least 30%, at least 40%, at least 50%, at least 60%, at least 70%, at least 80%, at least 90%, at least 100%, at least 200%, at least 300% as compared to the expression or activity of the genes or gene products in the absence of the one or more test compounds. Methods to measure changes in expression of a gene or a gene product are known to one of ordinary skill in the art.

Pharmaceutical Formulations and Dosage Forms

When employed as pharmaceuticals, the inhibitors of the present invention can be administered in the form of pharmaceutical compositions. These compositions can be administered by a variety of routes including oral, rectal, transdermal, subcutaneous, intravenous, intramuscular, and intranasal, and can be prepared in a manner well known in the pharmaceutical art.

This invention also includes pharmaceutical compositions which contain, as the active ingredient, one or more of the compounds of Formula I or any other isoMnSOD inhibitor as described above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, or about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as a chemotherapeutic, anti-viral agents, antibiotics, antibodies, immune suppressants, anti-inflammatory agents, FAAH inhibitors, and the like. In some embodiments, the compounds of the invention are formulated in combination with one or more chemotherapeutics and other agents used for treating cancer or heart failure.

In order that the invention disclosed herein may be more efficiently understood, examples are provided below. It should be understood that these examples are for illustrative purposes only and are not to be construed as limiting the invention in any manner.

EXAMPLES

Example 1

*E. coli* Transformation and Recombinant MnSOD Exon3-Deleted Isoform Protein Extract The pRSET-B/MnSOD Exon3-deleted isoform recombinant DNA contained as an insert a 600 nucleotide DNA fragment from human MnSOD Exon3-deleted isoform cDNA from coding nucleotide 95 to 695 (Genbank Accession #: X07834) that was amplified by PCR and cloned into the NdeI-Hind3 site of pRSET-B (Invitrogen). BL21/pLysS cells (Invitrogen) were transformed with pRSET-B/MnSOD Exon3-deleted isoform and the expression of the MnSOD Exon3-deleted isoform cDNA was induced in a 20 ml culture by addition of 1 mM IPTG at $OD_{600}$ 0.6 for 2.5 hrs. Pelleted cells were washed 1× in buffer A (70 mM Mannitol, 200 mM sucrose, 5.0 mM KCL, 1.0 mM EDTA, 0.1 mM DTPA, 1.0 mM EGTA pH 7.4) and stored frozen. To facilitate lysis, cell pellets were thawed for 10 min, refrozen, and lysed for 20 min at room temperature in 1 ml of B-Per detergent (Pierce) containing 1/10 vol of 5M NaCl and bacterial protease inhibitors (Sigma). The cell extract is centrifuged at 7 K rpm for 5 min, the supernatant removed, and the pellet was re-extracted with 500 µL of B-PER and centrifuged. B-Per extractions of the bacterial pellet were continued to fully solubilize the recombinant MnSOD Exon3-deleted isoform.

Example 2

Transient Transfections

For cDNA transient transfections into mammalian cell lines, cells were grown in MCDB131 medium containing 10% FBS. For transfection, $4 \times 10^6$ cells were released from the tissue culture plate using 0.05% Trypsin/EDTA (GIBCO/BRL) and resuspended in 1 ml of MCDB medium containing 10% FBS, which was then gently mixed with 4 ml of MCDB medium without serum containing 5 μg of recombinant DNA complexed with DMRIE-C (20 μL), according to manufacturer's instructions (BRL). After an incubation of cells with the DNA/DMRIE-C complex for 20 min, the cells were pelleted at 1000 g for 5 min, washed once with MCDB 10% FBS and replated in MCDB containing 10% FBS. This transfection procedure resulted in high viability of cells without potential toxicity by DMRIE-C. At different time points (24, 48 and 72 hrs), cells were recovered with 0.25% trypsin, 1 mM EDTA, counted and aliquoted in tubes at $\sim 1 \times 10^6$ cells for western immunoblot analysis.

Example 3

Western Immunoblot Analysis

Samples were lysed in 2× Laemmli SDS lysis buffer (4.0 ml 10% SDS, 2.0 ml glycerol, 1.2 ml Tris 6.8, 2.8 ml $H_2O$; add 1 μl of β-mercaptoethanol (14.4M) per 1 ml of lysis buffer) and boiled for 5 min. The proteins were separated on an 12% polyacrylamide SDS denaturing gel, and electroblotted onto a nitrocellulose PVDF membrane overnight at 20 volts. Membranes were blocked for 1 hr in TBS with 0.1% Tween 20 and 1% BSA; this blocking buffer was also used throughout the immunoblotting procedure. Proteins were detected using the affinity pure, rabbit polyclonal antibody, anti-MnSOD Exon3-deleted isoform, directed to 12 amino acids flanking the human MnSOD E2/E4 splice junction peptide rabbit polyclonal antibody, anti-MnSOD Exon3-deleted isoform, a pan-MnSOD pAb (Upstate Biotechnology), mouse anti-HNE (Genox), or goat anti-8-epi-PGF2a(isoprostane) (Oxford Biomed). The secondary antibodies were HRP conjugated (Santa Cruz Biotechnology) and were detected using Femto Western blotting procedure (Pierce) following manufacturer's instructions.

Example 4

Drug Inhibition Method

Figure 4:
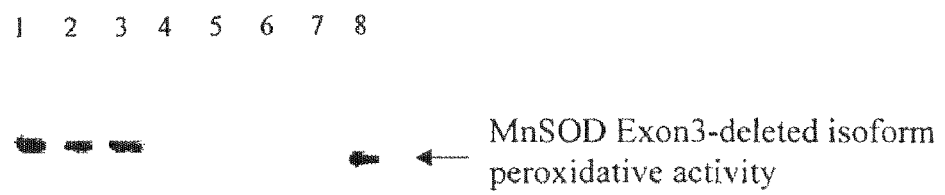
FIG. 4: In vitro analysis of the effect of test compounds on the peroxidative activity of the MnSOD-Exon3-deleted isoform according to Example 4. Lane 1: no treatment; Lane 2: arachidonoyl-glycine; Lane 3: arachidonoyl-3-hydroxy-γ-aminobutyric acid (GABA); Lane 4: arachidonoyl-dopamine; Lane 5: eicosapentaenoyl (EPA)-dopamine; Lane 6: docosahexaenoyl (DHA)-dopamine; Lane 7: C18:4(ω-3)-dopamine; Lane 8: arachidonoyl-ethanolamide.

Each test compound was prepared by mixing 5 μL of a 1 mM test compound stock solution in ethanol with 5 μL of 0.1 M KOH, followed by the addition of 5 ml of TBS for a final concentration of 1 μM test compound. Equal amounts of native protein extracts from pancreatic mitochondria (obtained according to the protocol of Example 5) were loaded in separate wells and resolved in a 7% PAGE gel without SDS, electrotransferred to PVDF and divided into strips. Each PVDF strip was incubated with 1 μM of test compound in TBS for 30 minutes, washed twice in TBS for 20 minutes, and the peroxidative activity of isoMnSOD was measured by incubation of each strip with 1 mM $H_2O_2$ in 0.4 ml of the luminol solution contained within the Femtomole chemiluminescence assay kit (Pierce) and exposed to x-ray film (FIG. 4). Compounds in lanes 4-7 (arachidonoyl-dopamine; eicosapentaenoyl (EPA))-dopamine; docosahexaenoyl (DHA)-dopamine; C18:4(ω-3)-dopamine; respectively) were found to inhibit peroxidative activity more significantly than the other compounds.

Example 5

Isolation and Lysis of Pig Pancreatic Mitochondria

All procedures were carried out at 4° C. Mitochondria were obtained from a liquid nitrogen powder of one pig pancreas (~8 g), which was resuspended in 15 ml of buffer A containing following protease inhibitors: 1 μg/ml aprotinin, 1 μg/ml pepstatin A, 1 μg/ml chymostatin A, 2 μg/ml leupeptin, 2 μM benzamide hydrochloride, and 11M phenylmethylsulfonyl fluoride. Tissue was broken with a Potter homogenizer and the homogenate was centrifuged for 10 min at 800 g to remove cell debris. The supernatant was centrifuged at 10,000 g from 15 min to recover mitochondria. The mitochondrial pellet was washed twice with a hand held Dounce homogenizer and mitochondria were stored frozen. Mitochondria were lysed by slowly adding 1 ml of M-Per (Pierce) containing 1/10 vol 5M NaCl and 1/10 vol Buffer A. The mitochondrial lysate was subsequently clarified by centrifugation for 10 min at 2000 g.

Example 6

Peroxidase Activity

Peroxidase activity was monitored using luminol-dependent chemiluminescence. Luminol stock solution (32.2 mM) was prepared by dissolving 5.7 mg/mL of luminol in 1 N NaOH. A working stock was prepared daily by adding 0.1 mL of luminol stock to 19.9 mL of 1 M sodium phosphate buffer, pH 7.0; 0.1 mL of working solution was added to 0.5-mL aliquots of the sample to be assayed for a final concentration of 23 μM luminol. $H_2O_2$ (100 mM in 0.2 M sodium phosphate, pH 7) was prepared from concentrated (30%) $H_2O_2$ daily; 100 μL was added to 0.5-mL aliquots to be assayed for a final concentration of approximately 1 mM. For peroxidase assays the luminol and $H_2O_2$ were added to samples simultaneously and the chemiluminescence was measured in an automated luminometer (Stratagene). The maximum chemiluminescence reading (mV) during a 30-s period was recorded. Changes in peroxidase activity could easily be detected using a luminometer, but it can have the drawback of being susceptible of trace amount of contaminating transition metals. Thus a method was developed to measure the peroxidative activity of MnSOD Exon3-deleted isoform directly on nitrocellulose filters.

Recombinant and mammalian detergent extracts of native mitochondrial proteins were separated in a 7% PAGE gel without SDS containing 375 mM Tris pH 8.2 at 100 volts for 1.5 hr. After electrotransfer of proteins to nitrocellulose using transfer buffer without SDS, peroxidative activity was measured directly upon the filter by their incubation with 0.5 ml of the Femtomole luminol solution (Pierce) containing 1 mM $H_2O_2$ and exposing to x-ray film or other means of detecting chemiluminescence.

The peroxidative activity of MnSOD Exon3-deleted isoform was also measured using a standard dot blot assay. MnSOD proteins were immunoprecipitated from either a bacterial or mammalian protein extract solubilized by 1 ml of B-Per containing 1/10 vol 5 M NaCl and 1/10 vol Buffer A using 5 μg of the polyclonal rabbit anti-MnSOD antibody (UpState Biotechnology). Immune complexes were allowed to form overnight at 4° C. Twenty microliters of Protein G Plus-Agarose conjugate (Santa Cruz Biotechnology) was added, and after a 1-h incubation period, the complex was washed four times with RIPA buffer (PBS with 1% Nonidet P-40/ 0.5% sodium deoxycholate/0.1% SDS). The solution was mixed with 100 µl of TBS, pipeted onto HybondC nitrocellulose in a dot blot manifold, vacuumed dried, and 0.5 ml of 0.1 M citrate buffer pH 3.5 was added to the agarose beads to release and transfer the MnSOD Exon3-deleted isoform onto nitrocellulose. The filter is washed with TBS and analyzed by chemiluminescence as described above.

Example 7

Induction of MnSOD Alternative Splicing and MnSOD Exon3-Deleted Isoform Synthesis by Anti-Fas Antibody Induction of MnSOD Exon3-Deleted Isoform In Cells by the Addition of Anti FAS CH-11 Antibody:

The human prostatic cell line, PC3, was grown in complete MCDB 131 medium containing 10% FBS. Cells were passed 24 hours prior to treatment. Two hours prior to treatment, the medium was replaced with MCDB medium containing 1% FBS. 1×10 (5) PC-3 cells treated with anti-Fas mAb (IPO-4, 1 mg/ml) for different times, and cellular SDS extracts were prepared as described herein. The anti-Fas mAb induced expression of isoMnSOD.

Example 8

Antisense Targeting of isoMnSOD Induction During Fas-Induced Apoptosis in Prostate Cancer PC3 Cells Blocks Caspase 9 Activation The Fas (CD95) receptor is a type I transmembrane protein that mediates cell death and can be engaged by the agonist anti-Fas antibody, CH-11. PC-3 cells are deficient for the recessive oncogene, p53, and thus, Fas-mediated apoptosis in PC-3 cells is p53-independent. Fas-mediated apoptosis in PC3 cells is not robust, but does exhibit release of mitochondrial pro-apoptotic factors within two hours after Fas-ligation, such as cytochrome c, which is necessary for protease-activation cleavage of caspase-9 and nuclear DNA degradation (Gewies, A. et al., (2000). Cancer Res 60, 2163-8).

We found that isoMnSOD, as well as normal MnSOD, were induced within one hour after ligation and engagement of the Fas receptor by the agonist Fas antibody, mAb CH-11 in PC-3 (data not shown). Induction of isoMnSOD expression exhibits a similar time course as the release of pro-apoptotic cytochrome c from mitochondria and activation of caspase 9 (Gewies, A. et al., (2000). Cancer Res 60, 2163-8). In order to determine if isoMnSOD is necessary for caspase 9 activation, we targeted the isoMnSOD mRNA at the MnSOD E2/E4 splice junction using antisense and as a control, reverse sense MnSOD oligodeoxynucleotide (ODN). There was a loss of both isoMnSOD and caspase 9 activation in cells treated with MnSOD E2/E4 antisense ODN.

Example 9

Doxorubicin Induces isoMnSOD Expression

Mitochondrial oxidative stress has been implicated as causative for the energy-loss and increased level of premature cell death (e.g. apoptosis and/or necrosis) that is observed in Doxorubicin (DOX)-induced cardiac dysfunction. Although the antineoplastic action of DOX in dividing cells is due to its inhibition of Topoisomerase II, Doxorubicin accumulates within the mitochondria of differentiated cardiomyocytes and leads to excessive production of the superoxide free radicals or anions. Doxorubicin itself is not pro-oxidant, but requires redox-activation of its quinone moiety to a semiquinome. The semiquinome of DOX reacts with oxygen, which in turn generates superoxide radicals, while at the same time, the DOX quinome moiety is regenerated. This process is called redox cycling and leads to toxic levels of superoxide free radicals and overwhelms the capacity of the endogenous MnSOD antioxidant defense system. Consistent with this, a transgenic animal overexpressing MnSOD can suppress Doxorubicin-induced cardiotoxicity.

Preparation of Adult Cardiomyocyte Explants.

Adult cardiomyocytes were isolated and purified following the combination of perfusion techniques (Borg et al. Recognition of extracellular matrix components by neonatal and adult cardiac myocytes. Dev Biol. 1984; 104:86-96) and an attachment procedure (Bugaisky L B, Zak R. Differentiation of adult rat cardiac myocytes in cell culture. Circ Res. 1989; 64:493-500) as described by Sil et al. (Sil et al. Myotrophin in human cardiomyopathic heart. Circ Res. 1993; 73:98-108). Briefly, after rats (5 weeks old) were killed by decapitation, the hearts were aseptically excised and residual blood was removed. The heart was perfused in Joklik's medium (containing Joklik's minimal essential medium, 25 mmol/L glutamic acid, 30 mmol/L taurine, and 1 mmol/L adenosine) without recirculation on a modified Langendorff apparatus for approximately 10 minutes at 37° C. The perfusion was then continued for 30 minutes at the same temperature, with recirculation in Joklik's medium containing collagenase type II (100 U/mL). After perfusion, the ventricles were cut into small pieces and tritulated in 0.05% Trypsin/EDTA for 10 min. Cardiac explants were cultured overnight on laminin-coated (20 µg per well) 35-mm six-well plates in medium 199 containing 5% FBS, 5 mM creatine, 2 mM L-carnitine, and 5 mM taurine. Explants were treated with doxorubicin (Sigma) shortly after plating for 24 hrs at 1 mM.

Figure 3:
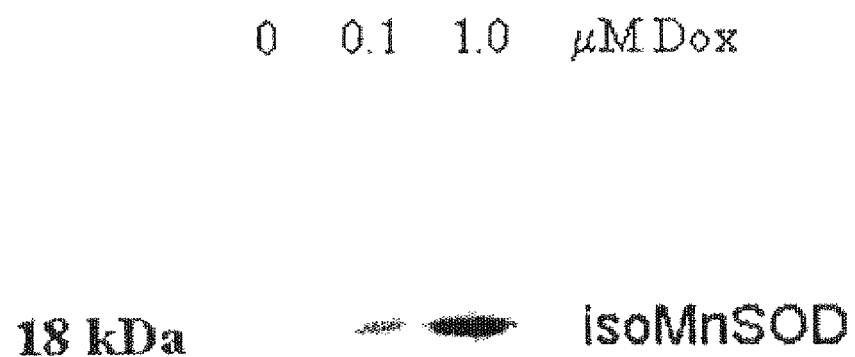
FIG. 3: Doxorubicin induces the expression of isoMnSOD according to Example 10. Lane 1: no treatment; Lane 2: 0.1 µM doxorubicin; Lane 3: 1.0 µM doxorubicin. Membrane was probed for isoMnSOD protein by Western Blot.

Cardiomyocytes only express the normal MnSOD mRNA and protein, but incubation of adult heart explants for 3 days with 0.1 nM to 1.0 µM Doxorubicin in AdvDMEM 2% FBS induced isoMnSOD expression (FIG. 3). isoMnSOD expression was analyzed by Western Blot. isoMnSOD expression was positively correlated with apoptotic activation of caspase 3.

Example 10

Expression of isoMnSOD Leads to Isoprostane and/or HNE Protein Modification

BL21 cells were transformed with pRSET-B/isoMnSOD. Proteins were analyzed for 8-epi-PGF2α-modified proteins using an antibody that recognizes 8-epi-PGF2α. The expression of isoMnSOD induced the modification of proteins by the isoprostane, whereas the empty vector failed to modify the proteins with 8-epi-PGF2α (data not shown).

PC12 were transfected with either empty vector (pcDNA3.1) or a vector carrying the cDNA of isoMnSOD (pcDNA3.1/isoMnSOD) with its mitochondrial targeting signal. The DNA was transfected with DMRIE-C (GIBCO/BRL) for 30 hours. Proteins were analyzed by Western blot for isoprostane modification. Isoprostane protein modification was induced when isoMnSOD was expressed, but not when only the empty vector was used (data not shown).

The human prostate cell line, PC3, were transfected with either empty vector or pcDNA3.1/isoMnSOD. Proteins were analyzed for HNE modification using an antibody that recognizes HNE modified proteins. HNE modified proteins were increased in response to the expression of isoMnSOD as compared to the negative control (empty vector; data not shown).

PC12 cells were transiently transfected for 30 hours with either empty vector or a vector carrying the isoMnSOD cDNA. HNE modification of proteins was detected via Western Blot. Proteins were modified by HNE in response to the transfection of isoMnSOD, but not in response to the empty vector (data not shown).

Example 11

Inhibition of Drug-Induced Toxicity

Doxorubicin is used to induce cardiomyopathy and cardiotoxicity as described in Arola et al. (*Cancer Research*, 60:1789-1792). Rats, ~300 g, are treated once with doxorubicin by IP injection using 2.5, 5, 10, and 15 mg/kg doxorubicin. Animals are sacrificed two days afterwards and tissue is stored frozen at −70° C. The dosage of arachidonoyl-dopamine to treat rats is at 7.5 mg/kg and 15 mg/kg and injected IP at the time=0, 6 hrs, and 24 hrs after doxorubicin injection. A working solution of arachidonoyl-dopamine is prepared by adding an equal amount (vol/vol) of the stock solution (40 mM arachidonoyl-dopamine in ethanol) to 0.1 M KOH and then bringing the final volume of 0.2 ml with PBS. The rats are analyzed for changes in cardiotoxicity and physiology following treatment of isoMnSOD inhibitor. MnSOD expression and isoMnSOD expression is analyzed in the treated rats by Western Blot and Immunostaining.

Mitochondrial proteins from heart, kidney, liver and pancreas are examined by measuring the in vitro peroxidative activity of the MnSOD Exon3-deleted isoform using the ROS-activity blots in parallel with the combined immuneprecipitation/dot blot analysis of the peroxidative activity. Both procedures are based upon the chemiluminescence detection of ROS by the oxidation of luminol. Secondly, western immunoblot analysis of mitochondrial proteins are analyzed for both native MnSOD and MnSOD Exon3-deleted isoform proteins, as well as the level of covalent modification of proteins by reactive lipid peroxidation byproducts, such as HNE and 8-epi-PGF2α. Total cellular proteins are also be examined by western immunoblot, probing for markers for premature cell death including activation of caspase-9 and -3 cleavage, downstream protein targets of activated caspase proteases, such as cleavage of PARP and degradation of cellular proteins linked to necrotic premature cell death, including cardiac connexin-43. The inhibitor reduces the markers of cell death as compared to a negative control.

In order to assess heart function, a Langendorf isolated perfused heart preparation and left ventricular developed pressure (systolic-diastolic), the maximal rate of left ventricular pressure development (dP/dt max) and the minimal (relaxation) rate of left ventricular pressure development (dP/dt min), or the coronary flow are measured. An inhibitor of drug-induced toxicity reduces the heart toxicity.

Example 12 isoMnSOD Inhibitors Inhibit Peroxidase Activity

F10 medium was used throughout the procedure. Pancreas (8 grams) from a 3 kilo pig was minced, washed twice, and 1 g of tissue was resuspended in 5 ml of F10 medium. An equal volume of either 2 μM arachidonoyl-dopamine, eicosapentaenoyl (EPA)-dopamine, docosahexaenoyl (DHA)-dopamine, C18:4-dopamine or arachidonoyl-serotonin was added and each pancreatic explant was cultured for 1 hr at 37° C. in 5% $CO_2$ tissue culture incubator. Explants were stored frozen at −70° C. Tissue was homogenized in Buffer A at 4° C. and mitochondria was isolated by differential centrifugation and stored frozen at −70° C. Peroxidative assay of native mitochondrial extracts analyzed by the ROS-activity blot. Results are shown in FIG. 1. Docosahexaenoyl (DHA)-dopamine (lane 4), C18:4ω-3-dopamine (lane 5), and arachidonoyl-serotonin (lane 6) inhibited the mitochondiral peroxidase activity. Arachidonoyl-dopamine (lane 2), eicosapentaenoyl (EPA)-dopamine (lane 3) did not inhibit peroxidase activity to the same effect.

Example 13

Detection of Inhibitors Bound to isoMnSOD

Figure 2:
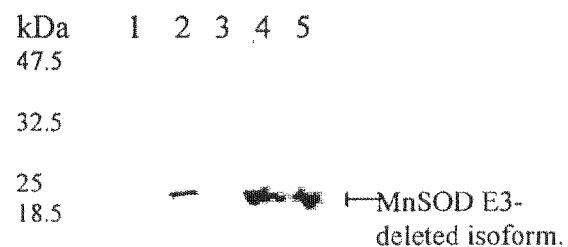
FIG. 2: Covalent modification of the MnSOD-Exon3-deleted isoform by isoMnSOD inhibitors according to Example 14. A. Detection of dopamine-modification—Lane 1: no treatment; Lane 2: arachidonoyl-dopamine; Lane 3: eicosapentaenoyl (EPA)-dopamine; Lane 4 docosahexaenoyl (DHA)-dopamine; Lane 5: C18:4(ω-3)-dopamine. B. Detection of serotonin-modification—Lane 1: no treatment; Lane 2: arachidonoyl-serotonin.
Figure 2:
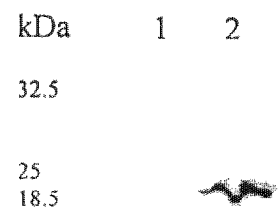

Covalent modification of the MnSOD-Exon3-deleted isoform was measured by a combined immuneprecipitation/western blot analysis. Immunoblots for detecting AA-DA, EPA-DA, DHA-DA, C18:4(ω-3)-DA adducts were performed using anti-dopamine rabbit polyclonal (Chemicon) and anti-serotonin goat polyclonal antibodies (ImmunoStar), respectively. After immunoprecipitating using an antibody against the inhibitor, isoMnSOD was detected as described above. Arachidonoyl-dopamine (AA-DA) docosahexaenoyl-dopamine (DHA-DA), C18:4-dopamine, and arachidonoyl-serotonin (AA-serotonin) were found to be able to bind to isoMnSOD (FIG. 2A and FIG. 2B).

Example 14

Identification of isoMnSOD Inhibitors Using Isoprostane Production as a Marker

A cell is transfected with an empty vector or a vector encoding for isoMnSOD. A test compound is added to the cell in vary concentrations ranging from 1 nm to 1 M. The levels of isoprostanes production are measured using an enzyme immunoassay for isoprostanes (Oxford Biomedical Research, Product No. EA 84). The amount of free isoprostanes are compared between a cell that has and has not been contacted with a test compound. A decrease in free isoprostanes is found indicating that the test compound is an isoMnSOD inhibitor.

Example 15

Identification of isoMnSOD Inhibitors using NHE Production as a Marker

A cell is transfected with an empty vector or a vector encoding for isoMnSOD. A test compound is added to the cell in vary concentrations ranging from 1 nm to IM. The levels of HNE production or HNE protein modification are measured using an enzyme immunoassay or antibody for HNE. The amount of HNE or HNE protein modifications are compared between a cell that has and has not been contacted with a test compound. A decrease in HNE or HNE protein modifications is found indicating that the test compound is an isoMnSOD inhibitor.

Example 16

Characterization of Reactive Oxygen Species by isoMnSOD

The activity of isoMnSOD was analyzed using recombinant produced isoMnSOD and. isoMnSOD produced in bacterial BL21 cells was isolated and analyzed via Western Blot and also for reactive oxygen species (ROS)-generating activity. "ROS-generating activity gel" was measured (FIG. 5A, left panel) and western immunoblot (FIG. 5A right panel) analyses of recombinant MnSOD E3-deleted isoform was analyzed. The results demonstrates the congruence of the peroxidative activity and immunoreactivity of the recombinant MnSOD E3-deleted isoform.

Characterization of the MnSOD E3-Deleted Isoform in Pig Pancreatic Mitochondria.

Figure 5:
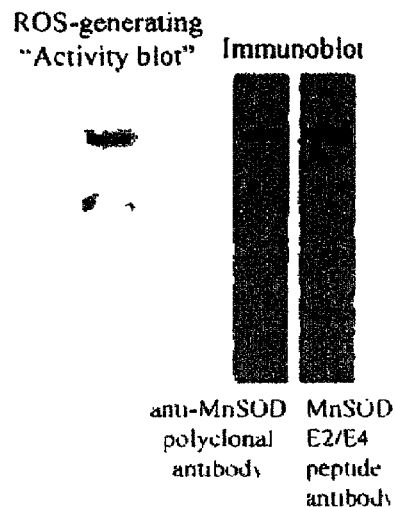
FIG. 5: Characterization of isoMnSOD peroxidative activity. A. Reactive Oxygen Species generating activity gel (left panel) and western immunoblot (right panel) analysis of recombinant isoMnSOD, produced in bacterial BL21 cells. B. Characterization of the isoMnSOD protein in pig pancreatic mitochondria. Four lanes each of 25 µg of pig pancreatic mitochondrial proteins were separated by a 7% PAGE without SDS. Measurement of the antioxidant, native MnSOD superoxide dismutase activity was performed in-gel (lane 1). The additional three gel-lanes were electrotransferred to nitrocellulose and analyzed for peroxidative analysis using the "ROS-generating activity blot" (lane 2) and protein assignment by Western immunoblot analysis using the anti-MnSOD (lane 3) and anti-MnSOD E2/E4 peptide (lane 4) polyclonal antibodies. C. The peroxidative activity of pig isoMnSOD (left lane) is supershifted by pre-incubation with 1 µg of the anti-MnSOD polyclonal antibody prior to native gel electrophoresis (right lane).
Figure 5:
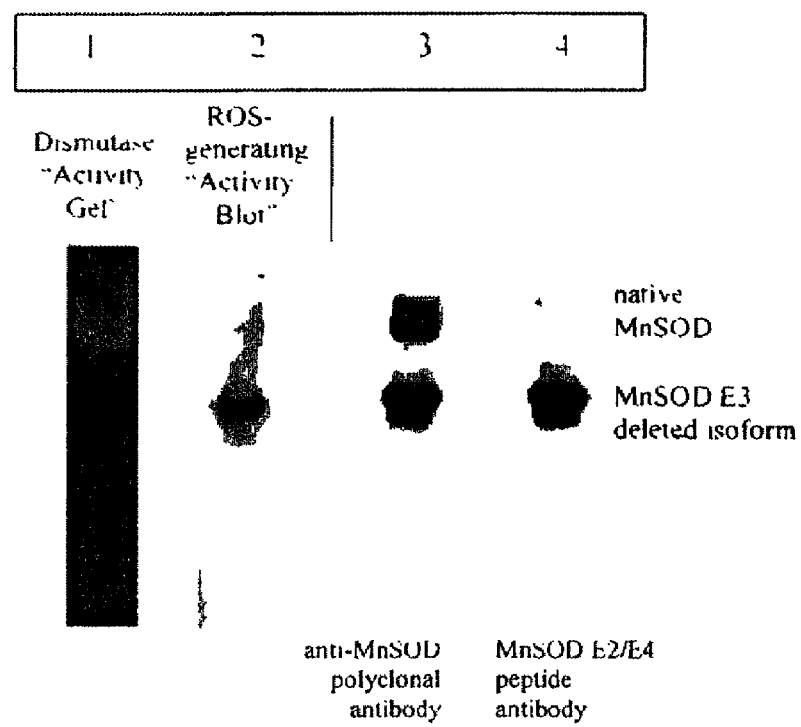
Figure 5C:

Four lanes each of 25 µg of pig pancreatic mitochondrial proteins were separated by a 7% PAGE without SDS. Measurement of the antioxidant, native MnSOD superoxide dismutase activity was performed in-gel (FIG. 5B, lane 1). The additional three gel-lanes were electrotransferred to nitrocellulose and analyzed for peroxidative analysis using the "ROS-generating activity blot" (FIG. 5B, lane 2) and protein assignment by Western immunoblot analysis using the anti-MnSOD (FIG. 5B, lane 3) and anti-MnSOD E2/E4 peptide (lane 4) polyclonal antibodies. Comparing lanes 1 and 2 shows that the dismutase, antioxidant activity strictly corresponds to native MnSOD (FIG. 5B, lane 3; upper complex), whereas the peroxidative activity is confined to the MnSOD E3-deleted isoform (FIG. 5, lanes 3 and 4; lower band). To further confirm that the peroxidative activity is due to the activity of isoMnSOD, the pig extract was preincubated with 1 µg anti-MnSOD polyclonal antibody prior to native gel electrophoresis (FIG. 5C, right lane). The antibody shifted the ROS-generating band produced by isoMnSOD as compared to the control (FIG. 5C, left lane), which indicates that the ROS-generating activity is due to the presence and activity of isoMnSOD. Thus, the results demonstrated that isoMnSOD is able to generate reactive oxygen species, which is in contrast to MnSOD, which has antioxidant activity.

Example 17

Reporter Gene System to Analyze Compounds for Toxicity

The test reporter system utilizes a recombinant DNA construct that contains an ATG start codon in MnSOD Exon 2, an in frame fusion of a genomic fragment spanning MnSOD Exon 2 to Exon 4, but which also harbors a mutant MnSOD Exon 3, (i.e. frameshift mutation), to a B-galactosidase gene, or Green Fluorescence Protein ("altMnSODreport"). However, alternative splicing and skipping of MnSOD (coding) Exon 3 will result in a fusion protein comprising a short stretch of MnSOD E2 and E4 coding sequences N-terminal to a reporter protein; the MnSODE2E4 amino acid sequence is 20 amino acids and should not interfere with the expression of the reporter. Normal splicing of the MnSOD transcript, with retention of MnSOD E3, generates a mRNA that contains a stop codon in E3 sequences upstream of the reporter and will therefore prematurely terminate translation, and fail to generate a fusion protein a signal, and result in no reporter signal.

The genomic fragments are isolated using PCR. The source of the MnSOD genomic DNA is human BAC RP11-280121 or mouse BAC RP23 64P12. The genomic structure of MnSOD, nucleic acid sequence of isoMnSOD, and the amino acid sequence of isoMnSOD are described in U.S. Pat. No. 6,737,506, which is herein incorporated by reference in its entirety.

The reporter is tested in prostate cancer cells, PC3, that are treated with Fas CH-11 mAb because Fas induces dysregulation of the normal MnSOD splicing pathway and production of isoMnSOD and this model system is clinically relevant. PC3 cells are transiently transfected with the reporter construct. Greater than 80% of cells are transfected using 5 µg of recombinant DNA complexed to DMRIE-C lipofectant (BRL) and added to trypsinized cells. Once cells have reattached overnight, transfected cells are treated with Fas CH-11 mAb. Using Green Fluorescence Protein as the reporter, the increase in fluorescence is monitored over real-time due to dysregulation of the normal MnSOD splicing pathway and production of the MnSODE2E4reporter fusion protein.

The Toxicology Screen is validated with two tests to assure that the reporter signal is due to a fusion of MnSOD E2/E4 sequence to the reporter and not MnSOD E2/E3/E4 sequences. First, transfected cells are treated with antisense ODN targeted directed to the MnSOD E2/E4 junction; sense and reverse sense ODNs serve as controls. Inactivation of the MnSOD E2/E4/reporter mRNA ODN by MnSOD E2/E4 antisense ODN results in the loss of a reporter signal or loss of GFP fluorescence, while control ODNs has no effect. The second control assay is to perform a western immunoblot analysis, using an antibody directed against the MnSOD E2/E4 peptide junction. In addition, the expression of the reporter gene is examined using antibodies against the reporter protein; an antibody against MnSOD protein (Stressgene) will not detect the short MnSOD E2/E4 amino acid sequence in the fusion protein. The correct fusion protein is detected by the MnSODE2/E4 peptide antibody and confirmed by an antibody against the reporter protein.

The endogenous expression of the MnSOD and isoMnSOD proteins is also examined. This verifies that there is induction of isoMnSOD upon treatment with Fas mAb, CH-11. The steady state levels of isoMnSOD is quantitatively measured relative to the normal MnSOD and as a control, subunit II of the Cytochrome C Oxidase, the terminal electron acceptor in the mitochondrial electron transport system. The induction of apoptosis is characterized using antibodies to caspase 9 and 3.

Testing of Drugs for Toxicity

Drugs are tested alone or in combination in cancerous or diseased cells and in healthy cells. The compounds are added to cells comprising the reporter gene system. The induction of the reporter is characterized in the absence and the presence of the drug(s).

Breast cancer cell line, MDA-MB-435, Her-2/neu overexpressing (ATCC), fibroblast cells lines NIH3T3 and B104, which are NIH3T3 cells transfected with the rat ErbB2/Her2 oncogene, and normal primary cells (Clonetics; rat cardiomyocytes, donated by Kathryn Maschhoff, MD PhD, Neonatology, University of Pennsylvania) are treated with doxorubicin alone and in combination with the rat ErbB2/Her2 17.6.4 monoclonal antibody, which downregulates the human and rat Her2 receptor (Zhang et al., 1999)(Oncogene), and Herceptin™ (Genentech). It is also determined if the Her2 mAbs induces isoMnSOD expression in untransfected cells and cells transfected with altMnSODreport. A dose-response curve is established, using western immunoblot analysis of the isoMnSOD protein and the expression of the reporter construct. A similar analysis is performed for doxorubicin treatment of cells. Both treatments are analyzed for their effects on mtDNA stability by Southern hybridization analysis, induction of lipid peroxidation by immunodetection of HNE-modified proteins, and induction of apoptosis by activation of caspases 9 and 3. Doxorubicin causes an increase in expression of altMnSOD report.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety. U.S. provisional application Ser. No. 60/473,458, filed May 28, 2003 is incorporated herein by reference in its entirety.

What is claimed is:

1. A method of treating heart failure induced by the administration of an anthracycline drug, comprising administering to an individual in need thereof a therapeutically effective amount of an isoMnSOD inhibitor, wherein the isoMnSOD inhibitor is selected from the group consisting of: arachidonoyl dopamine, eicosapentaenoyl dopamine, docosahexaenoyl dopamine, C18:4($\omega$-3)-dopamine, and combinations thereof.

2. The method of claim 1 wherein said heart failure comprises non-ischemic heart failure.

3. The method of claim 1, wherein said anthracycline is selected from the group consisting of: doxorubicin, epirubicin, daunorubicin, idarubicin, and combinations thereof.

* * * * *